US009023085B2

(12) United States Patent
Strippgen

(10) Patent No.: US 9,023,085 B2
(45) Date of Patent: May 5, 2015

(54) DYNAMIC SURGICAL IMPLANT

(71) Applicant: Walter E. Strippgen, Berthoud, CO (US)

(72) Inventor: Walter E. Strippgen, Berthoud, CO (US)

(*) Notice: Subject to any disclaimer, the term of this patent is extended or adjusted under 35 U.S.C. 154(b) by 43 days.

(21) Appl. No.: 14/071,189

(22) Filed: Nov. 4, 2013

(65) Prior Publication Data

US 2014/0058511 A1 Feb. 27, 2014

Related U.S. Application Data

(63) Continuation-in-part of application No. 13/551,691, filed on Jul. 18, 2012, now Pat. No. 8,608,784, which is a continuation of application No. 12/975,577, filed on Dec. 22, 2010, now Pat. No. 8,231,624.

(51) Int. Cl.
*A61B 17/80* (2006.01)
*A61F 2/28* (2006.01)
(Continued)

(52) U.S. Cl.
CPC ... *A61F 2/28* (2013.01); *A61F 2/44* (2013.01); *A61F 2/4455* (2013.01); *A61F 2/446* (2013.01); *A61F 2/4465* (2013.01); *A61F 2/4684* (2013.01); *A61B 17/7055* (2013.01); *A61B 17/8085* (2013.01); *A61B 17/826* (2013.01); *A61F 2002/30062* (2013.01); *A61F 2002/30113* (2013.01); *A61F 2002/30224* (2013.01); *A61F 2002/30235* (2013.01); *A61F 2002/30451* (2013.01); *A61F 2002/30462* (2013.01); *A61F 2002/30472* (2013.01); *A61F 2002/30518* (2013.01); *A61F 2002/30522* (2013.01); *A61F 2002/30784* (2013.01); *A61F 2002/3084* (2013.01); *A61F 2002/3093* (2013.01); *A61F 2002/30971* (2013.01); *A61F 2002/4415* (2013.01); *A61F 2002/4475* (2013.01); *A61F 2002/4485* (2013.01); *A61F 2002/449* (2013.01); *A61F 2002/4495* (2013.01); *A61F 2310/00011* (2013.01); *A61F 2310/00017* (2013.01);
(Continued)

(58) Field of Classification Search
CPC .......................... A61B 17/8085; A61B 17/826
See application file for complete search history.

(56) References Cited

U.S. PATENT DOCUMENTS 390,393 A * 10/1888 Norris ................................ 5/120
3,706,473 A * 12/1972 Mullen .................... 297/452.16
(Continued)

FOREIGN PATENT DOCUMENTS

WO WO 2005/037150 4/2005
WO WO 2005/112835 12/2005

OTHER PUBLICATIONS

Harms, "Screw-Threaded Rod System in Spinal Fusion Surgery" in SPINE: State of the Art Reviews, vol. 6, No. 3, Sep. 1992 (pp. 541-575).
(Continued)

*Primary Examiner* — Nicholas Woodall
(74) *Attorney, Agent, or Firm* — Sheridan Ross P.C.

(57) ABSTRACT

A surgical implant device capable of conforming to a variety of surface topographies facilitates the growth and regeneration of site to which the device is applied. The device employs a plurality of elongate members supporting a column of discrete, rotatable elements in contact with each adjacent element. Anchor plates secure the respective ends of the elongate members, such anchor plates attachable to bone. The implant device provides and ordered array of individually rotatable elements to form a surface that permits bodily fluids to pass therethough.

20 Claims, 15 Drawing Sheets

(51) Int. Cl.
*A61F 2/44* (2006.01)
*A61B 17/70* (2006.01)
*A61B 17/82* (2006.01)
*A61F 2/46* (2006.01)
*A61F 2/30* (2006.01)

(52) U.S. Cl.
CPC ............... *A61F2310/00023* (2013.01); *A61F 2310/00179* (2013.01); *A61F 2310/00215* (2013.01); *A61F 2310/00227* (2013.01); *A61F 2310/00281* (2013.01); *A61F 2310/00299* (2013.01); *A61F 2310/00317* (2013.01); *A61F 2310/00329* (2013.01); *A61F 2310/0097* (2013.01); *A61F 2310/00976* (2013.01); *A61F 2310/00916* (2013.01)

(56) References Cited

U.S. PATENT DOCUMENTS

| | | | |
|---|---|---|---|
| 4,089,071 A | | 5/1978 | Kalnberz et al. |
| 4,192,547 A | * | 3/1980 | Geier ................ 297/452.63 |
| 4,502,161 A | | 3/1985 | Wall |
| 4,773,402 A | | 9/1988 | Asher et al. |
| 4,839,215 A | | 6/1989 | Starling et al. |
| 4,887,595 A | | 12/1989 | Heinig et al. |
| 4,955,911 A | | 9/1990 | Frey et al. |
| 5,108,397 A | | 4/1992 | White |
| 5,113,685 A | | 5/1992 | Asher et al. |
| 5,346,492 A | | 9/1994 | Morgan |
| 5,443,483 A | | 8/1995 | Kirsch |
| 5,681,310 A | | 10/1997 | Yuan et al. |
| 5,756,127 A | | 5/1998 | Grisoni et al. |
| 5,766,176 A | | 6/1998 | Duncan |
| 6,060,641 A | * | 5/2000 | Manolidis ................ 128/898 |
| 6,066,175 A | | 5/2000 | Henderson et al. |
| 6,077,076 A | | 6/2000 | Comfort |
| 6,086,613 A | | 7/2000 | Camino et al. |
| 6,127,596 A | | 10/2000 | Brown et al. |
| 6,523,680 B2 | | 2/2003 | Guldenfels |
| 6,827,743 B2 | | 12/2004 | Eisermann et al. |
| 7,229,441 B2 | | 6/2007 | Trieu et al. |
| 7,344,539 B2 | | 3/2008 | Serhan et al. |
| 7,651,497 B2 | | 1/2010 | Michelson |
| 7,655,047 B2 | | 2/2010 | Swords |
| 7,658,766 B2 | | 2/2010 | Melkent et al. |
| 7,662,185 B2 | | 2/2010 | Alfaro et al. |
| 7,670,375 B2 | | 3/2010 | Schaller |
| 7,824,433 B2 | | 11/2010 | Williams |
| 8,231,624 B1 | | 7/2012 | Strippgen |
| 8,608,784 B2 | | 12/2013 | Strippgen |
| 8,795,377 B2 | * | 8/2014 | Engqvist et al. ........... 623/17.19 |
| 2004/0199252 A1 | | 10/2004 | Sears et al. |
| 2004/0249464 A1 | | 12/2004 | Bindseil et al. |
| 2005/0065516 A1 | | 3/2005 | Jahng |
| 2005/0113855 A1 | | 5/2005 | Kennedy, II et al. |
| 2006/0052873 A1 | | 3/2006 | Buck et al. |
| 2006/0184246 A1 | | 8/2006 | Zwirkoski |
| 2007/0073293 A1 | | 3/2007 | Martz et al. |
| 2007/0100454 A1 | | 5/2007 | Burgess et al. |
| 2008/0161855 A1 | | 7/2008 | Serhan et al. |
| 2009/0162643 A1 | | 6/2009 | Dubrow et al. |
| 2009/0292365 A1 | | 11/2009 | Smith et al. |
| 2010/0057208 A1 | | 3/2010 | Dryer et al. |
| 2010/0063548 A1 | | 3/2010 | Wang |
| 2011/0035008 A1 | | 2/2011 | Williams |

OTHER PUBLICATIONS

Lowery, et al., "Titanium Surgical Mesh for Vertebral Defect Replacement and Intervertebral Spaces", Manual of Internal Fixation of the Spine, 1996, Chapter 10, pp. 127-146.

Official Action for U.S. Appl. No. 12/975,557, mailed Feb. 1, 2012 9 pages.

Official Action for U.S. Appl. No. 12/975,557, mailed Apr. 27, 2012 10 pages.

Notice of Allowance for U.S. Appl. No. 12/975,557, mailed Jun. 25, 2012 5 pages.

Official Action for U.S. Appl. No. 13/551,691, mailed Mar. 14, 2013 10 pages.

Official Action for U.S. Appl. No. 13/551,691, mailed Jun. 24, 2013 7 pages.

Notice of Allowance for U.S. Appl. No. 13/551,691, mailed Oct. 23, 2013 7 pages.

* cited by examiner

DYNAMIC SURGICAL IMPLANT

This U.S. Non-Provisional Patent application is a Continuation-in-Part of U.S. patent application Ser. No. 13/551,691 filed Jul. 18, 2012, which is a Continuation of U.S. patent application Ser. No. 12/975,577 filed Dec. 22, 2010, which is now U.S. Pat. No. 8,231,624, the entire disclosures of which are hereby incorporated by reference in their entireties.

FIELD OF THE INVENTION

The present disclosure relates generally to a device and method of use for an implantable apparatus for use in surgery. More specifically, the present disclosure relates to a conformable yet semi-rigid material for implanting into a patient and stabilizing, for example, an anatomical feature such as a bone fracture site, pedicle, or intervertebral disk space.

BACKGROUND OF THE INVENTION

It is current practice in orthopedic surgery to use plate and/or rod systems for joining portions of a broken bone, or for fusion of portions of separate bones. Such systems are composed essentially of plates, rods and screws for aligning and holding the bone portions in a desired position relative to one another. Plate and rod systems have usefulness in the spine, and have general skeletal use on the flat surfaces of bones, such as the scapula and the pelvis by way of example, and for use on tubular bones, such as the humerus, radius, femur, and tibia.

Currently known plating systems present disadvantages to patients and surgeons as they do not contemplate and/or allow for mass transfer to and from a site directly below or surrounding the plate. Thus, conventional plates typically impede the regeneration and osteosynthesis of the bone or tissue they are intended to heal. Additional problems associated with plating systems have included hardware breakage, hardware loosening, insufficient flexibility particularly over time, inability to gain adequate fixation, unnecessary additional weight, and other problems related to implant and recovery of the patient. One particular problem is "distraction pseudoarthrosis" where the plate will not allow the bone portions to come together over time resulting in a failure to get solid bone healing. These occurrences may cause problems, be associated with surgical failure, and require further surgical procedures to repair the damage, remove the failed hardware, and/or to reattempt stabilization of the boney anatomy.

Plates and rods are usually provided to the surgeon for use in sets having a range of sizes so as to provide for such features as biological variability in size, the numbers of segments to be joined, and the length of the portions of bone to be joined. By way of example, it would be common for a plating system for use on the anterior cervical spine and for joining from two to five vertebrae to comprise of from forty to sixty plates. This requires manufacturers to make a large number of different plates, resulting in increased manufacturing costs and inventory costs and increased costs for hospitals to stock large numbers of plates. Further, in the event that a plate is used and another of its kind is needed before it can be replaced, the ability to provide to a patient the best care could be compromised.

Known plate and rod systems additionally experience problems in connection with those procedures where bone grafts are placed between vertebral bodies to achieve an interbody fusion which heals by a process called "creeping substitution." In this process, dead bone at the interfaces between the graft and the adjacent vertebra is removed by the body, as a prelude to the new growth of bone forming cells and the deposition of new bone. While the plates and rods allow for proper alignment of the vertebrae and their rigid fixation, they can therefore, at the same time unfortunately, hold the vertebrae apart while the resorption phase of the creeping substitution process forms gaps in the bone at the fusion site with the result that the desired fusion does not occur. Such failure in an attempted fusion is known as pseudoarthrosis. A similar phenomenon occurs at the interface of a fractured bone's fragments and is known as non-union. When such a failure occurs, the hardware itself will usually break or become loosened over time requiring further surgery to remove the broken hardware and to again attempt fusion or fracture repair.

There has been a long-felt and unmet need for an implant system which provides for required levels of strength, shock absorption, resistance to stresses and strain, and yet still allows for compliance and flexibility in order to wrap or accommodate various non-planar implant sites, while still allowing for adequate mass transfer to and from the implant site.

SUMMARY OF THE INVENTION

The present invention comprises a method and apparatus for a surgical implant system which further contemplates and allows for circulation of air and liquids essential for growth, regeneration, and proper function of a bioactive area to which the apparatus is to be applied. The invention comprises the ability to allow for sufficient breathability and passage of certain elements, thus enabling bone and tissue growth beneath, around, and/or within the implant, and further provides sufficient structural support in various directions. In one embodiment, the present invention comprises a malleable mesh-like device, similar to a breathable bandage, which is capable of conforming to a variety of non-planar implantation sites while still providing sufficient stability and resistance to certain forces.

In one embodiment, the present invention comprises a device for use in intervertebral connection, including a "ligament" or attaching member. In this embodiment, the device is secured by bone fasteners, such as, for example, first and second shoulderless bone fasteners connecting to the first end portion of the ligament and the second end portion of the ligament, respectively. The ligament has a conformable portion, which is formed by a series of filaments (e.g. wires) and segments (e.g. cylinders) having a hollow center through which a filament passes.

In another embodiment, a surgical implant for strengthening a bone or joint is provided which comprises a plurality of individual parallel spaced wires extending from and affixed to a first anchor member and a second anchor member. In this particular embodiment, each individual parallel spaced wire has a plurality of generally circular and/or cylindrical members surrounding each of the wires and the generally circular members are freely rotatable about the wires. In an alternative embodiment, the plurality of wires and plurality of generally circular members form a fabric-like structure that permits liquids to flow therethrough and permits bone ingrowth when implanted adjacent to a patient's bone.

In yet another embodiment, the plurality of wires and plurality of generally circular members comprise at least one biocompatible material selected from the group consisting of ceramic, PEEK, titanium, stainless steel, stainless steel alloys and titanium alloys. The plurality of wires and plurality of generally circular members may comprise a resorbable synthetic material.

In one embodiment, the wires have a diameter of about 0.01 mm to about 2 mm and the generally circular members have a diameter of approximately 0.250 inches and approximately 0.500 inches.

In yet another embodiment, the plurality of generally circular members contact adjacent generally circular members on an adjacent individual spaced wire.

In yet another embodiment, each of the first and second anchor members has at least two apertures adapted to receive a screw.

In one embodiment, the plurality of wires comprise one of ceramic, titanium, stainless steel, stainless steel alloys and titanium alloys and the plurality of generally circular members comprises PEEK.

In another embodiment, the plurality of wires and plurality of generally circular members have resilient and damping properties. For example, the generally circular members may be comprised of a material which is capable of absorbing a certain amount of force or impact and deflecting or straining to a certain degree without plastically deforming.

In one embodiment, neither the plurality of wires nor the plurality of generally circular members are interlocked with one another. In yet another embodiment, the generally circular members comprise a plurality of through holes formed therein.

In an alternative embodiment, a plurality of parallel pins is oriented perpendicular to a plurality of generally circular members. A first end and a second end of one pin are affixed to a first anchor member, and a first end and a second end of another pin are affixed to a second anchor member. The generally circular members have a first aperture at a first end and a second aperture at a second end. These apertures allow a pin to perpendicularly pass through such that the generally circular members may rotate freely about the pin.

To form an interlocking mesh, the anchored pins pass through the apertures of one end of a plurality of generally circular members. Non-anchored pins, which are arrayed between the anchored pins, pass through the apertures of alternating ends of a plurality of generally circular members. The result is an interlocking mesh of the plurality of parallel pins and the plurality of generally circular members. This mesh may articulate about the pins such that the present invention may easily wrap around an anatomical feature.

In one embodiment, an appliance is provided for covering a surgery site of a bone in vivo. The appliance comprises a flexible member adapted for contacting the bone surface of a patient to promote healing of the bone surface and surrounding bone and/or tissue. In this embodiment, the member has a first side and a second side adapted to face toward and away from the bone, respectively. The member further comprises a plurality of wires and a plurality of generally circular members forming a fabric-like structure that permits liquids to flow therethrough and permits bone ingrowth when implanted adjacent to a patient's bone. The member has at least two closure edges proximate each other when the member is wrapped around the bone and includes connecting means, engaging the at least two closure edges, for connecting the closure edges to firmly hold the member around a bone. Connecting means may include, for example, various staples, fasteners, clasps, sutures, pins, zippers, welds, crimping elements adapted for use with an appliance or implant.

In an alternative embodiment, a pliable structure for use in surgery is provided which comprises a pliable structure having a first face side and a bone interface side and including a multiplicity of recesses provided that permit in growth of bone therethrough. The structure has generally uniformly shaped arcuate members positioned around a plurality of wires spaced generally parallel to each other to form adjacent rows of rotatable rows of arcuate members. In this embodiment, the structure further has a substantially uniform configuration about an interior portion thereof, at least two periphery anchor sites adapted to connect to another portion of the member, or connect directly to a bone surface via one of a bone screw, bone staple or bone adhesive. As used herein, the term arcuate refers generally to members that have at least one curved, rounded, or partially-rounded surface.

In another embodiment, the structure of the present invention is fabricated of biocompatible metals and metal alloys selected from the group consisting of titanium, titanium alloys, cobalt-chrome alloys and stainless steel. In another embodiment, the multiplicities of recesses are too small to receive a bone screw. In yet another embodiment, the first face side and the bone interface side are interchangeable.

The following references related to spinal implants, cage bodies, methods and devices for spinal correction, and intervertebral implants and plates are known to be relevant to the field of the present invention and are hereby incorporated by reference in their entireties: U.S. Patent Application Publication No. 2010/0057208 to Dryer et al., WO/2005/037150 to Martz et al., WO/2005/112835 to Serhan et al., U.S. Patent Application Publication No. 2007/0073293 to Martz et al., U.S. Patent Application Publication No. 20100063548 to Wang, U.S. Pat. No. 7,662,185 to Alfaro et al., U.S. Patent Application Publication No. 2009/0162643 to Dubrow et al., U.S. Pat. No. 7,651,497 to Michelson, U.S. Pat. No. 6,077,076 to Comfort, U.S. Pat. No. 6,827,743 to Eisermann et al., U.S. Pat. No. 7,655,047 to Swords, U.S. Pat. No. 4,502,161 to Wall, U.S. Pat. No. 4,089,071 to Kalnberz et al., U.S. Pat. No. 6,066,175 to Henderson et al., U.S. Patent Application Publication No. 2006/0052873 to Buck et al., U.S. Pat. No. 5,766,176 to Duncan, U.S. Pat. No. 5,346,492 to Morgan, U.S. Pat. No. 5,443,483 to Kirsch, U.S. Pat. No. 7,658,766 to Melkent, U.S. Pat. No. 6,086,613 to Camino et al., U.S. Pat. No. 7,670,375 to Schaller, U.S. Pat. No. 4,773,402 to Asher et al., U.S. Pat. No. 4,887,595 to Heinig et al., U.S. Pat. No. 5,113,685 to Asher et al., U.S. Patent Application Publication No. 2009/0292365 to Smith et al., U.S. Patent Application Publication No. 2007/0100454 to Burgess et al., U.S. Pat. No. 7,344,539 to Serhan et al., U.S. Pat. No. 7,229,441 to Trieu et al., U.S. Pat. No. 6,127,596 to Brown et al., U.S. Patent Application Publication No. 2008/0161855 to Serhan et al., and U.S. Pat. No. 4,955,911 to Frey et al.

There has been a gradual acceptance of interbody fusion as a procedure for a number of spinal disorders. Interbody fusion procedures may employ the use of surgical mesh tubes, see for example "Chapter 10: Titanium Surgical Mesh for Vertebral Defect Replacement and Intervertebral Spacers", Gary L. Lowery and Jurgen Harms, Manual of Internal Fixation of the Spine, edited by John S. Thalgott and Max Aebi, Lippincoll-Raven Publishers, Philadelphia, 1996, which is incorporated herein by reference.

While devices for use in interbody fusion which comprise a mesh or porous material are known, there remains a long-felt need for a device that offers the advantages of conventional bone plates without the obstruction of mass transfer and tissue growth associated with certain prior art devices. For example, U.S. Pat. No. 7,651,497 to Michelson, which is hereby incorporated by reference in its entirety, discloses various segmentable plates for application in reconstructive surgeries which may be contoured or shaped by a surgeon. Michelson, however, fails to disclose a device that is conformable to a surgical worksite and that further facilitates bone and tissue regeneration within, through, or proximal to the device. The present invention contemplates various features and structures disclosed in Michelson which further comprise novel features and aspects of the present invention as shown and described herein.

One embodiment of the present invention comprises an array or series of generally cylindrical components disposed on wires or a series of elongate devices of pliable material and further bounded by a first and second anchor device or plate at the first and second longitudinal ends of the pliable material. First and second anchor devices comprise points of attachment for the wires or elongate devices and further provide for the ability to anchor or secure the present invention to bone or a portion of the human anatomy. In one embodiment, the first and second anchor device each comprise at least two through holes suitable for accommodating a variety of surgical screws and similar fastening devices. In an alternative embodiment, the present invention comprises a variety of ports or apertures throughout the device wherein surgical screws or fastening/anchoring devices may be employed. For example, in addition to or in lieu of anchor points which may be provided on the first and second anchor devices, anchor points may be provided at various locations interspersed between the generally cylindrical components. In this embodiment, numerous anchor points are provided which allow for the device to be securely positioned in a variety of orientations. In one embodiment, prescribed eyelets or grommets are provided at interstitial locations within an area defined by the generally cylindrical components. These eyelets may be comprised of a variety of materials, including, but not limited to, the group consisting of: surgical stainless steel, titanium, silicon, glass, quartz, plastic, metal and metal alloys, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, SiO1, SiO2, silicon carbide, silicon nitride, polyacrylonitrile (PAN), polyetherketone, polyetheretherketone (PEEK), polyimide, an aromatic polymer, and an aliphatic polymer. Furthermore, eyelets or grommets provided in the area defined by the generally cylindrical components, as well as through holes provided on the first and second anchor devices, may be offset or angled to provide for a crossed configuration of bone screws and a resulting stable engagement of the device to a bone as further shown and described in U.S. Pat. No. 7,651,497 to Michelson, which is hereby incorporated by reference in its entirety.

In one embodiment, the wires on which the generally cylindrical components are disposed are substantially malleable or pliable to allow for the present invention to be placed on, over, and/or generally conform to a variety of non-planar surfaces and objects. Thus, in one embodiment, the present invention provides for a surgical implant with improved characteristics over currently known plating mechanisms in that it is readily adaptable to various three-dimensional non-planar surfaces, yet still provides for adequate rigidity and resistance to forces applied in tension, compression, and, to a certain degree, torsion. Furthermore, the present invention provides a device which fosters growth, healing, and redevelopment of bone, tissue, and material located beneath and proximal to the device. By providing a structure that does not cover a target area in such a manner as to generally prevent or prohibit substantial amounts of mass transfer (i.e. does not prevent the transfer of air, blood, and fluid), the present invention facilitates healing and repair of bone and other materials situated beneath and proximal to the present invention.

By providing a stacked arrangement of generally cylindrical components, one embodiment of the present invention provides the ability to resist compression forces in one orientation, yet provides flexibility in an opposite (e.g. 90° orientation). While the present invention contemplates use in securing bone fracture sites, embodiments of the present invention may be utilized in procedures such as interbody fusion, cage fixation, and spinal fixation. The present invention offers the advantage of being able to at least partially conform to a non-planar work site in cage fixation procedures. The present invention offers such functionality while still providing sufficient resistance to forces applied in the z-axis.

The material used to construct the body of the present invention may be a non-porous material, such as surgical steel, titanium, or related alloys. In one embodiment, 316 stainless metal is utilized to form portions of the device, such as end plates, wires, and generally cylindrical components. In one embodiment, generally cylindrical components are employed wherein the components are of approximately 0.370 inch diameter and are approximately 0.500 inches in length. Wires are preferably of a diameter between approximately 0.02 and 0.10 inches. In a preferred embodiment, wires are of a diameter between 0.03 and 0.035 inches. In a more preferred embodiment, wires are of a diameter of approximately 0.033 inches. However, one of ordinary skill in the art will recognize that the present invention is not bounded by these disclosed embodiments. Indeed, it is contemplated that the devices employing nanotechnology will comprise features of significantly smaller dimensions than these embodiments. Additionally, larger devices are also contemplated by the present invention and may be utilized, for example, in large non-human mammals or species.

In a preferred embodiment, the wires are securely welded to the end plates. However, one of skill in the art will recognize that the wires may be attached to the end plates in a variety of ways, so long as attachment is secure and there is minimal risk of the wires becoming dislodged from the plates before, during, or after implantation. In one embodiment, metal parts of the present invention are malleable and not hardened.

In yet another embodiment, a single cylinder may have more than one wire passing through its center, thus providing a way for adjacent columns of cylinders to remain in desired proximity with each other. As one of skill in the art will appreciate, different diameter sized cylinders can be employed to form an overall expanse of columns and rows of cylinders strung on wires so that a fabric appearance is achieved, but one not necessarily uniform in every respect.

In one embodiment, metal surfaces (including but not limited to the inner surfaces of the cylinders) of the present invention are finished in a satin finish to improve bone growth into the surface. In an alternative embodiment, surfaces are roughened or unprocessed to enhance bone growth. For example, methods and devices as described in U.S. Patent Application Publication No. 2009/0292365 to Smith et al., which is hereby incorporated by reference, may be utilized.

A plurality of openings may be provided on the surface of the present invention to enable mass transfer through the device. In one embodiment, openings are provided that allow the bone growth material to grow through at least a portion of the present invention and fuse with vertebral members and other portions of the indigenous anatomy. In various embodiments, openings may be provided at regular intervals, organized in rows or columns, distributed radially, or staggered randomly. In one particular embodiment, openings consist of spatial gaps between generally cylindrical components and that are subject to repositioning and resizing based on a certain degree of freedom of movement of the generally cylindrical components with respect to each other.

In one embodiment, the present invention ensures that bone-building material will have osseous tissue growing through it from at least the side of the covering which faces the bone to achieve complete ossification thereof and complete integration of the ingrown osseous tissue with the osseous tissue of the surrounding bone region.

In another embodiment, a member, which can have absorbable material associated therewith, acts to reinforce the healing site and is intended to seat tightly against the bone on all sides. While the member can be secured to the bone, for example, by means of invasive fastening elements, such as pins, which must traumatically engage the bone, in one embodiment, avoidance of hammering the pins into the bone, which typically causes pain to the patient, can be alleviated by having connecting means that secures together two portions of the member so as to fit the member (e.g. bent around the bone), thus also avoiding the need to ever subsequently remove pins, etc., after the bone has healed. Thus, in one embodiment, a flexible member has a surface that faces the bone and has two closure edges which permit the member to be wrapped around the bone at the surgery site and to be firmly closed in the region of the surgery site by means of connector elements.

Therefore, the present invention contemplates an appliance for covering a surgery site of a bone in vivo, comprising a flexible member adapted for contacting the bone surface of a patient to promote healing of a bone surface. In one embodiment, the member has a first side and a second side, the first side being adapted to face toward said bone, and the second side adapted to face away from said bone. The member has at least two closure edges proximate each other when said member is wrapped around bone. Furthermore, connecting means are provided, engaging the at least two closure edges, for connecting said closure edges to firmly hold the member around the bone.

In a particular embodiment, the present invention comprises a surgical implant adapted for use with the human wrist. For example, an implant is provided which is adapted to cover or be applied to at least a portion of the circumference of a human wrist (i.e. the combined circumference of the radius and ulna). In one embodiment, the implant allows for at least some degree of natural rotation of the wrist bones about a longitudinal axis of the forearm, while simultaneously provided adequate support for the wrist and resistance to, for example, moment forces that may be applied to the wrist and/or forearm. Additionally, the device provides various additional benefits of the present invention wherein the device is readily conformable to a variety of shapes/topography and further allows for the exchange of air and fluid through the device, thereby promoting healing and regenerative functions.

In one embodiment, the present invention comprises an implant that provides the same or similar structural support to a bone plate as used in connection with a wrist, yet further allows for natural rotation of various features of the wrist as well as promoting healing, bone, and tissue growth in one or more areas directly beneath the device.

In one embodiment, the present invention comprises a non-surgical brace or device that is worn externally on a patient. For example, various features of the present invention may be incorporated within or used to form an externally-worn wrist support which prevents or minimized unwanted bending without overly prohibiting rotational movement of a wrist and components thereof.

The present invention, in one embodiment, comprises an implant for surgical use in humans or vertebrates, in particular for the replacement, for the partial replacement or for the strengthening of a damaged intervertebral disk or for the replacement, for the partial replacement or for the strengthening of an anatomical joint.

Such an implant should essentially correspond to the dimensions and the shape of the joint to be replaced or of the intervertebral disk to be replaced, have adequate biocompatibility with the surrounding tissue and especially comparable physical properties, in particular with respect to rigidity, elasticity, resilience and damping, and make possible unrestricted movement within the course of natural movement and have a long lifetime in order not to stress a patient by frequent implant changes.

To promote bone ingrowth into the implant, the outsides of the implants oriented toward the bone are preferably provided with a surface structuring. In one embodiment, the surface structuring comprises a variety of recesses. The recesses may be formed by providing generally circular grommets and/or by providing a stacked arrangement of generally cylindrical components with interstitial spaces therebetween.

In preferred embodiments of the present invention the device is able to be adapted, by a simple variation of wire and/or cylinder composition, spacing, size, etc. to affect its rigidity, elasticity and its resilience and internal damping, to conform to the desired characteristics or specifications of the corresponding joint or intervertebral disk to be replaced or to be supported.

Owing to internal friction of the wires and generally circular members, oscillations are effectively damped, such as are initiated from outside on the body system, intervertebral disk and/or joints by walking, running and especially by jumping. The fabric formed by the above described wire and generally circular member configuration is reliably greatly deformable yet supportive, a combination greatly desired for particular applications in bone surgery.

Materials which can be used to construct suitable embodiments are, in particular, alloys which contain, inter alia, as constituents in various quantitative proportions, titanium, cobalt, chromium, aluminum, vanadium, niobium and/or zirconium or stable plastics, as well as resorbable organic materials, in this case, inter alia, catgut, catgut chromium or collagen or else alternatively resorbable synthetic materials, such as organically degradable polymers, in this case, inter alia, Vicryl, Polysorb, Dexon, Piralac, Serafit, Bondek, Maxon or Panacryl.

The elasticity and damping and all other parameters (e.g. dimensions) are chosen according to the natural implants to be replaced.

In one embodiment, the device has the ability to adjust to the stresses due to elastic or plastic deformations without lasting damage owing to its flexibility and is insensitive to tilting and bending and imparts to the human or the vertebrate the ability to carry out bending, tilting and rotation and translation movements.

In certain embodiments, the implants may substantially be anatomically shaped, i.e. the dimensions and the shape of the implant should correspond essentially to the dimensions and the shape of the intervertebral disk to be replaced and/or of the anatomical joint to be replaced. However, for reasons of functionality in the production and in the incorporation of the implant it can also be advantageous under certain circumstances to choose another shape.

Under certain circumstances, the use of a material resorbable by the body can be useful in conjunction with various embodiments described herein. This is provided in the particularly advantageous embodiment in which the implant is colonized with stem cells or with endogenous cells which are cultured in the laboratory. The great advantage here is that the new implant connects strongly with the bone, while, for example, implants of plastic or other materials loosen with time and/or can lead to foreign body reactions. Here, the fabric forming the implant serves as a support structure. The fabric can comprise one or more of said resorbable materials and/or one or more of said biocompatible materials, in particular titanium, which then remains permanently in the body as a support structure.

The wire diameter and/or the dimensions of the generally circular members are chosen here in order to make possible a simple in-growth of the stem cells or of the endogenous cells.

The individual parameters may be determined empirically, such as by selecting: wire composition, length, flexibility, gauge, cylinder dimensions, composition, size relative to adjacent cylinders, etc. Thus the properties of the shaped article to be formed or of the implant to be formed on the properties of the intervertebral disk to be replaced or of the joint to be replaced can be optimally adjusted so that the implant optimally handles the local stress in its function and makes possible an improved transfer of force from the implant to the bone.

In one embodiment, the present invention comprises a generally non-flexible member. For example, an embodiment is contemplated where the stacked arrangement of generally cylindrical components is disposed on a series of parallel wires, yet is of a generally fixed shape. Such a fixed shape may include, for example, a flat plate or a device with a U-shaped cross-section. In this embodiment, the device may comprise enough flexibility to be spread or placed around a bone, but is generally not conformable to a shape substantially different from its original shape and position.

In one embodiment, a mesh system incorporating the fabric construction described herein comprises a general use skeletal mesh having a bottom surface for placement against bone portions, wherein a substantial portion of the bottom surface of the mesh is either flat or convex along the longitudinal axis of the mesh. It is appreciated that a lesser portion of the lower surface of the mesh may be otherwise shaped. The mesh of the present invention has a plurality of bone screw receiving holes which extend through the mesh, from the upper surface to the lower surface. The mesh and its component parts may be made of any implant quality material suitable for this purpose and suitable for use in the human body, such as, but not limited to, titanium or its alloys. The mesh and/or the associated components may be made of a bioresorbable material and may comprise or be coated at least in part with fusion promoting chemical substances, such as bone morphogenetic proteins and the like.

Bone screws are each insertable into a respective bone screw receiving hole for attaching embodiments of the present invention to bone. A locking element, preferably, but not necessarily, in the form of a screw, is engageable in the locking screw hole of the present invention and has a head formed to lock at least two of the bone screws to the present invention. In the preferred embodiment, the locking elements are pre-installed prior to use by the surgeon in a manner so as to not impede installation of the bone screws into the bone screw receiving holes.

Employing, for example, the breathable, supportive, yet flexible band-aide structure described herein, the problems previously associated with locking screws of the type applied after the insertion of the bone screws, including the problems of instrumentation to position and deliver to the mesh the locking means, backing out, breakage, stripping and mis-threading associated with the prior art more delicate locking screws resembling "watchmaker's parts," are substantially reduced and/or eliminated.

In a further embodiment of the present invention, a segmentable mesh system is disclosed combinable with the multiple lock and single-lock mesh system and the crossing screw teaching, as well as combinable with other novel features herein disclosed. The segmentable mesh system provides a single mesh, or a limited set of mesh, for aligning and maintaining bone portions in selected spatial relationship in which the mesh are manufactured so as to be strong in use, but separable into shorter lengths by the surgeon as needed, thereby eliminating the need to stock a multitude of mesh lengths.

In one embodiment, the present invention comprises cylinders that are at least partially adapted to receive one another. For example, in one embodiment, a first end of a cylinder comprises an open aperture which is generally circular when viewed in cross-section and a second end of the cylinder comprises a generally frustoconical nose portion which is adapted to fit within the first end of another cylinder. Thus, cylinders are adapted to fit at least partially within one another, providing for smoother bending/flexing of the device. In another embodiment, cylinders are adapted to receive at least a certain segment of another cylinder such that there is a slight telescoping or nesting of stacked cylinders. Thus, two cylinders on a single wire may translate within and with respect to one another (e.g. when a patient bends or stretches), but without complete disengagement of the cylinders.

According to one embodiment, an implant is provided with a textured bone and soft-tissue attachment surface that includes an implantable body having a micro-textured soft tissue ongrowth attachment surface thereon. The micro-textured surface is a roughened surface texture covering the macro-texturing for optimizing soft tissue ongrowth.

By way of example, for application in the spine, an embodiment of the segmentable mesh system of the present invention comprises a mesh that is capable of spanning multiple segments of a cervical spine and has predetermined separation zones. The separation zones may be positioned in a segmentable mesh such that when a portion of the segmentable mesh would be applied to the vertebrae, the remaining separation zones in the mesh, if any, would be supported by an underlying vertebra. In use, the surgeon would determine the appropriate mesh length needed and if the length needed was less than the length of the provided mesh, the surgeon would remove the unneeded portion of the mesh at the appropriate separation zone. By way of example, this procedure may be easily performed when the mesh is made of titanium or one of its alloys, as the properties of titanium are such that when the mesh is bent and then returned to its original position, a clean separation is made at the bend. The parts of the segmentable mesh that are being separated can be held to either side of the separation zone to ensure that a precise separation is effected. The separation zones of the segmentable mesh, by way of example, may comprise the mesh being scored along its upper, lower, or both upper and lower surfaces. The depth of such scores being dependent on the thickness of the mesh, and being sufficient to create surface notchings and a path of least resistance for the mesh separation, and yet of limited depth and shape, so as to not weaken the mesh so as to render it less than sufficiently strong for its intended use. It will be understood that reference to "mesh" is intended to include at least structures as depicted in the Figures and otherwise described herein, but is not necessarily to be construed as being so limited. For example, mesh-type structures known the prior art may be employed in concert with particular wire and/or cylinder constructs.

By way of example, for application to the anterior aspect of the cervical spine four segmentable mesh each having generally a similar length (for example sufficient to span five vertebrae, a length of from 80 to 120 mm), and each having different spacing between pairs of bone screw holes, could comprise a complete set of mesh allowing a surgeon to have all lengths and hole spacing needed to fuse from two to five vertebrae. While the described mesh may be separable into a multitude of usable portions, because of regulatory issues involving the identification of each implant with a distinct and singular implant identification number for tracking purposes. It may be desirable to configure the mesh of the present invention such that each mesh will yield only one usable portion.

The segmentable mesh system of the present invention also has application in reconstructive surgery. For example, during repair of a broken eye socket, the segmentable mesh system of the present invention can be used to align and maintain the broken bone portions in correct spatial relationship. The curved characteristic of an eye socket requires that the mesh used to repair the socket will match the curvature. The parallel wires of the present invention may be made of a malleable and/or flexible metal, such that it can more easily be contoured by the surgeon to the appropriate curvature. The 90° orientation of cylinders presents a structure capable of supporting tissue and bone. The ability to provide discrete, interlockable segments also provides significant advantages.

Therefore, while various mesh implants are known, they fail to disclose a number of novel features of the present invention. For example, U.S. Pat. No. 5,766,176 to Duncan discloses a formable mesh for use in osteosynthesis. Duncan fails to teach, however, a device suitable for use in spinal procedures which generally conforms to non-planar surfaces while still providing sufficient resistant to force in various directions.

In one aspect of the invention, a medical device is disclosed comprising a body structure having one or more surfaces having a plurality of nanostructured components associated therewith, such components similar to those depicted in the Figures. Such medical devices may comprise an implantable device, intracorporeal or extracorporeal device, a temporary or permanent implant, a stent, a vascular graft, an anastomotic device, an aneurysm repair device, an embolic device, a catheter, valve or other device which would benefit from a structured surface according to the teachings of the present invention. The plurality of nanostructured components may comprise, for example, a plurality of nanofibers or nanowires, as well as nano-scale cylinders positioned on such wires/fibres. The plurality of nanostructured components enhance one or more of adhesion, non-adhesion, friction, patency or biointegration of the device with one or more tissue surfaces of a body of a patient depending on the particular application of the device. The nanofibers (or other nanostructured components) on the surfaces of the medical device can optionally be embedded in a slowly-soluble biocompatible polymer (or other) matrix to make the nanofiber surfaces more robust. The polymer matrix can protect most of the length of each nanofiber, leaving only the ends susceptible to damage. The generation of water soluble polymers can be accomplished in a number of different ways. For example, polymer chains can be formed in situ in a dilute aqueous solution primarily consisting of a monomer and an oxidizing agent. In this case, the polymer is actually created in the solution and subsequently spontaneously adsorbed onto the nanofiber surfaces as a uniform, ultra-thin film of between approximately 10 to greater than 250 angstroms in thickness, more preferably between 10 and 100 angstroms.

The plurality of nanofibers or nanowires may comprise an average length, for example, of from about 1 micron to at least about 500 microns, from about 5 microns to at least about 150 microns, from about 10 microns to at least about 125 microns, or from about 50 microns to at least about 100 microns. The plurality of nanofibers or nanowires may comprise an average diameter, for example, of from about 5 nm to at least about 1 micron, from about 5 nm to at least about 500 nm, from about 20 nm to at least about 250 nm, from about 20 nm to at least about 200 nm, from about 40 nm to at least about 200 nm, from about 50 nm to at least about 150 nm, or from about 75 nm to at least about 100 nm. The plurality of nanofibers or nanowires may comprise an average density on the one or more surfaces of the medical device, for example, of from about 0.11 nanofibers per square micron to at least about 1000 nanofibers per square micron, from about 1 nanofiber per square micron to at least about 500 nanofibers per square micron, from about 10 nanofibers per square micron to at least about 250 nanofibers per square micron, or from about 50 nanofibers per square micron to at least about 100 nanofibers per square micron. The plurality of nanofibers or nanowires may comprise a material independently selected from the group consisting of: silicon, glass, quartz, plastic, metal and metal alloys, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, SiO1, SiO2, silicon carbide, silicon nitride, polyacrylonitrile (PAN), polyetherketone, polyimide, an aromatic polymer, and an aliphatic polymer.

The nanofibers or nanowires may be attached to the one or more surfaces of the body structure of the medical device by growing the nanofibers or nanowires directly on the one or more surfaces, or the nanofibers or wires may be attached to the one or more surfaces of the body structure by attaching (e.g., via a covalent linkage) the nanofibers or nanowires to the one or more surfaces using one or more functional moieties, for example. The body structure of the medical device may be made from a variety of materials, and the plurality of nanostructured components may optionally be incorporated into the material(s) of the body structure. The nanofibers (or other nanomaterial) may be stiffened by sintering the fibers together (or otherwise cross-linking the fibers, e.g., by chemical means) prior to incorporating the nanofibers into the material of the body structure to provide enhanced rigidity and strength. The medical device may further comprise one or more biologically compatible or bioactive coatings applied to the one or more nanostructured surfaces, and/or the nanofibers or nanowires may be incorporated into a matrix material (e.g., a polymer material) to provide greater durability for the fibers or wires.

One aspect of certain embodiments of the present invention is directed to systems and methods for spinal stabilization and fixation, useful in the replacement, reconstruction or augmentation of spinal ligament or bony tissues, and also in alternatively resisting or facilitating certain tensile and rotational loading applied thereto by spinal motion. As described herein, the particular varied configurations of embodiments comprise filaments or wires surrounded by generally freely rotatable cylinders (although other shapes, including polygonal structures having various flat or curved faces may be employed in addition to and/or in lieu of cylinders). Each individual filament/wire contains at least three, more preferably at least about five, and even more preferably at least about ten cylinders. Such filaments/wires are positioned in a generally parallel fashion with respect to each other. The respectively adjacent wires with associated hollow centered cylinders that are strung thereon are provided in desired proximity to a similar wire having similar cylinders. The particular lengths of each given cylinder can be the same or different as the particular overall desired structural characteristics dictate. For example, generally the smaller length of sequential cylinders will provide more flexible characteristics to an overall structure. Differently composed cylinders can be provided on a single wire or on separate wires to achieve certain desirable overall characteristics of the structure. For example, PEEK cylinders can be employed for certain flexibility advantages as compared to steel or titanium cylinders. If an entire row or column of cylinders (e.g. either strung on a single wire or adjacent to one another but on different adjacent wires) is composed of a similar material (such as a row of PEEK cylinders in a larger composite structure of steel wires/cylinders, thus resembling a fabric), then one can achieve desired points of increased or decreased flexibility to advance desired spinal motion in a patient into which such a structure is implanted. Due to the relative flexibility of the filament/wire, the structure is able to bend or flex far more in one direction than in a direction 90 degrees from such direction. Indeed, in a direction whereby the cylinders are stacked with their flat edges (e.g. top of cylinders facing each other) the structure demonstrates considerable load supporting capacity in such direction, while simultaneously being able to be twisted in a different plane, as well as bent or flexed in still another plane. For example, such a structure is able to be twisted in a fashion such that certain advantageous dynamic flexion is permitted, which is at least partially achieved by freely rotatable cylinders (although other shapes, including polygonal structures having various flat or curved faces). Thus, in one embodiment, the present invention comprises a device with a combination of flexibility in certain respects, and also certain stability, load bearing and rigidity in other respects (e.g. along distinct planes of movement).

In one form, an elongated implant comprising the above described structure is configured to span the intervertebral disc space with its ends attached to a respective vertebral body. The implant can have a substantially flexible yet substantially inelastic body with a low profile capable of conforming to the spinal anatomy. The anchors used to attach the ends of the implant to the vertebrae can be at least partially concealed in the vertebral body to which it is engaged, further reducing the profile of the device. Examples of suitable anchors include interference screws, suture anchors, bone screws, buttons, pin fasteners, and staples. It is further contemplated that the implant and anchors can be made from nonresorbable or resorbable material.

In one technique, the stabilization system can be attached to and stabilize the anterior portion of the spinal column. The stabilization system can also be attached to and stabilize the lateral or anterior-lateral portion of the spinal column. In another technique, the stabilization system is attached to a posterior portion of the spinal column via anchors engaged to the vertebrae at any one of a number of locations, including but not limited to the facets, pedicles, pars, transverse processes, or spinous processes. Preferred attachment techniques provide a low profile system that reduces exposure and contact with the adjacent anatomic structures.

Although one embodiment contemplates freely rotatable cylinders, various other shapes, including polygonal structures having various flat and/or curved faces and surfaces may be employed in the present invention. Additionally, weight and resorbability may be enhanced without significantly degrading the structural integrity of cylinders or similar devices by providing holes, knurling, or aeration in the cylinders or similar devices. Such devices are within the scope and spirit of the present invention.

The present invention is particularly useful for augmenting single or multi-level anterior interbody fusions. In some embodiments, the system is designed for use in the anterior lumbar region of the spine, and so is characterized by relatively larger ligament lengths (between 20 mm and 30 mm) in order to span the disc space. In other embodiments, the system is designed for use in the cervical region of the spine, and so is characterized by ligaments having relatively small lengths (such as between 12 mm and 15 mm) and small thickness (such as between 0.5 mm and less than 2 mm) in order to avoid exposure to the esophagus.

Generally, the bone fasteners of the present invention may be fastened to any portion of the anterior, lateral or posterior surface of the vertebral body. Preferably, however, the bone fasteners are fastened to the anterior surface in order to take advantage of the low profile produced by the system and to avoid a second surgery (posterior) in anterior interbody fusion procedures. In one embodiment, a "shoulderless" bone fastener may be employed that has no shoulder capable of seating upon the vertebral surface in a degree sufficient to prevent further driving of the bone fastener into the vertebral body.

One of skill in the art will recognize that invention is an open world, for which there are no rules; the education comes with time, that doesn't lend to schools; when there's a problem that disturbs, new answers would be found; there just aren't any books to read, so far they've not been bound; to create it takes a study time, there is no place to start; a study of the problem found, time must be set apart; invention comes because it's felt, a new design comes through; impossible can't match this strength, creation here comes true; the mind must understand the need, a reason to begin; to understand the purpose here, if efforts are to win; this takes determination set, a plus and minus score; a mind that searches for success must open up this door.

Various embodiments of the present invention, including for example, ligament aspects hereof, may be coated or embedded with one or more biologically or pharmaceutically active compounds such as cytokines (e.g., lymphokines, chemokines, etc.), attachment factors, genes, peptides, proteins, nucleotides, carbohydrates, cells or drugs.

In a preferred embodiment, bone fasteners are positioned in close proximity to the vertical portion of the endplate portions of the vertebral bodies to achieve a more secure fixation of the system due to the relatively higher hardness of the endplate region. Bone fasteners of the present invention may be fastened to the superior or inferior portions of the vertebral bodies near their endplates in the transition zone between the cortical and cancellous bone regions, preferably in some embodiments associated with a disk prosthesis component suitable as a replacement for a particular natural disk with an intervertebral connection system having a ligament whose length is designed for insertion of the bone fasteners into the endplates adjacent that natural disk.

In one embodiment, a surgical implant for strengthening a bone or joint is provided, the implant comprising a plurality of individual parallel spaced wires extending from and affixed to a first anchor member and a second anchor member. Each individual parallel spaced wire has a plurality of generally circular members surrounding it, the generally circular members being freely rotatable about a single one of the wires.

In another embodiment, an implant is provided with a plurality of wires and a plurality of generally circular members which form a fabric-like structure that permits liquids to flow therethrough and permits bone ingrowth when implanted adjacent to a patient's bone.

The plurality of wires and plurality of generally circular members may comprise at least one biocompatible material selected from the group consisting of ceramic, PEEK, titanium, stainless steel, stainless steel alloys and titanium alloys. In one embodiment, the implant comprises a plurality of wires and a plurality of generally circular members comprising a resorbable synthetic material.

In various embodiments, the implant has a plurality of wires with a diameter approximately between 0.01 mm and 2 mm and a length approximately between 0.060 inches and 0.500 inches.

In various embodiments, the implant has a plurality of wires comprising one of ceramic, titanium, stainless steel, stainless steel alloys and titanium alloys and PEEK.

In one embodiment, a device for covering a surgery site of a bone in vivo is provided, the device comprising a plurality of elongate flexible members having a first end, a second end, and a longitudinal axis therebetween. The longitudinal axis comprises a length that is significantly larger than a thickness of the elongate flexible member. A plurality of generally cylindrical members is disposed on each of the plurality of elongate flexible members, the cylindrical members comprising a hollow interior portion such that a portion of the longitudinal axis of one of the elongate flexible is allowed to pass and/or be threaded therethrough. The plurality of elongate flexible members and the plurality of generally cylindrical members form a structure that permits liquids (e.g. bodily fluids) to flow therethrough and permits bone growth when implanted adjacent to a bone. Additionally, the device has at least two predetermined locations for receiving a fastener for anchoring the device in a specific location.

The first ends of the elongate flexible members are secured to a first anchor plate and the second ends of the elongate flexible members are secured to a second anchor plate, the first and second anchor plates comprising an aperture for receiving a bone screw or similar fastening device.

The device may be further provided with at least two closure edges proximate each other when the device is wrapped around a bone and connecting means for engaging said at least two closure edges to firmly hold said member around said bone.

Invention is an open world
        For which there are no rules
    The education comes with time
        That doesn't lend to schools—
    When there's a problem that disturbs
        New answers would be found
    There just aren't any books to read
        So far they've not been bound—
    To create it takes a study time
        There is no place to start
    A study of the problem found
        Time must be set apart—
    Invention comes because it's felt
        A new design comes through
    Impossible can't match this strength
        Creation here comes true—
    The mind must understand the need
        A reason to begin
    To understand the purpose here
        if efforts are to win—
    This takes determination set
        A plus and minus score
    A mind that searches for success
        Must open up this door—

These and other needs are addressed by the various embodiments and configurations of the present invention. These and other advantages will be apparent from the disclosure of the invention(s) contained herein. The above-described embodiments, objectives, and configurations are neither complete nor exhaustive. As will be appreciated, other embodiments of the invention are possible using, alone or in combination, one or more of the features set forth above or described in detail below.

DETAILED DESCRIPTION OF THE FIGURES

Figure 1:
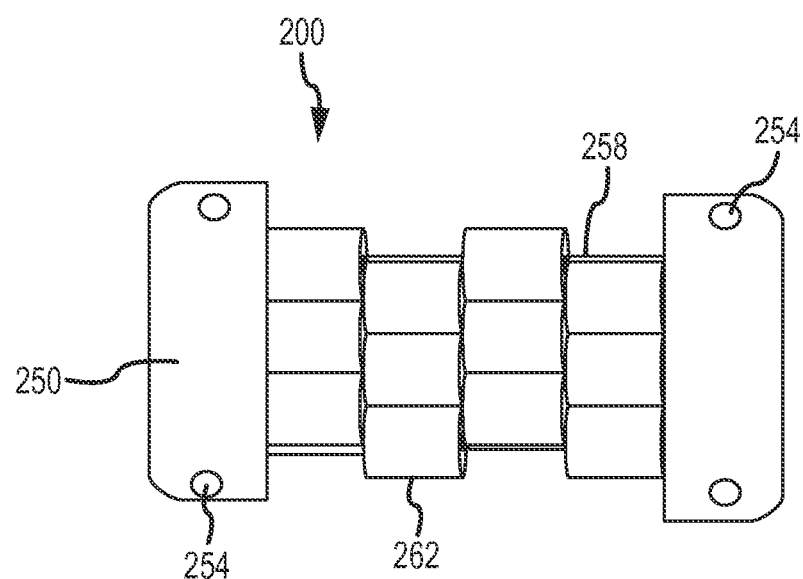
FIG. 1 is a top plan view of one embodiment of the present invention.

FIG. 1 depicts one embodiment representative of the present invention 200, wherein stacked or arranged components of generally cylindrical construction are provided. Anchor plates 250 are provided and further equipped with through holes 254 which can accommodate any number of known surgical screws or acceptable fixation devices (not shown, but 199 in FIG. 2). Anchor plates may be comprised of a variety of known surgical grade metals, including but not limited to surgical steel, titanium and titanium alloys. In addition to providing means for anchoring the present invention 200 to a bone or surgical area, anchor plates 250 define the terminal boundaries of wires 258 disposed between the anchor plates 250. In one embodiment, wires 258 are of sufficient strength to resist tension forces that may be applied, but are of a thin enough gauges to allow for manipulation and shaping of the device by hand. Wires 258 may be comprised of a variety of known surgical grade metals, including but not limited to surgical steel, titanium and titanium alloys. Disposed on the wires 258 is an array of generally cylindrical elements 262 which are generally free to rotate about an axis corresponding to the longitudinal axis of the wires 258. Although twelve stacked cylindrical components 262 are shown in FIG. 1, one of skill in the art will recognize that any number of these components 262 may be provided, either by selecting different sized cylindrical components 262 and/or by varying the dimensions of the device 200.

As shown and described, a stacked or threaded arrangement between elements 262 and wires 258 is provided. As used herein, threaded does not necessarily refer to a threaded member such as a screw or threaded hole, but more generally refers to an arrangement whereby at least a portion or length of one object (e.g. wire 258) extends through at least a portion of another object (e.g. element 262).

The stacked arrangement allows for a device which is capable of providing sufficient resistance to forces applied in the x-axis (i.e. tension and/or compression) as well as forces which may be applied in the z-axis (i.e. out of the page with respect to FIG. 1). However, the flexibility of the wires 258, the arrangement of the generally cylindrical components 262, and spacing which may be provided between the cylindrical components 262, allow for a user to mold or shape the device 200 to conform to a variety of anatomical features and surgical sites. In one embodiment, the device 200 is capable of being molded or re-shaped manually by a surgeon in operating room conditions. Thus, in one embodiment, the device 200 provides for a band-aid like surgical implant which functions similarly to conventional plates in some aspects (i.e. comprises the ability to resist certain forces) yet is readily conformable to a variety of shapes/topography and further allows for the exchange of air and fluid through the device 200.

Figure 2:
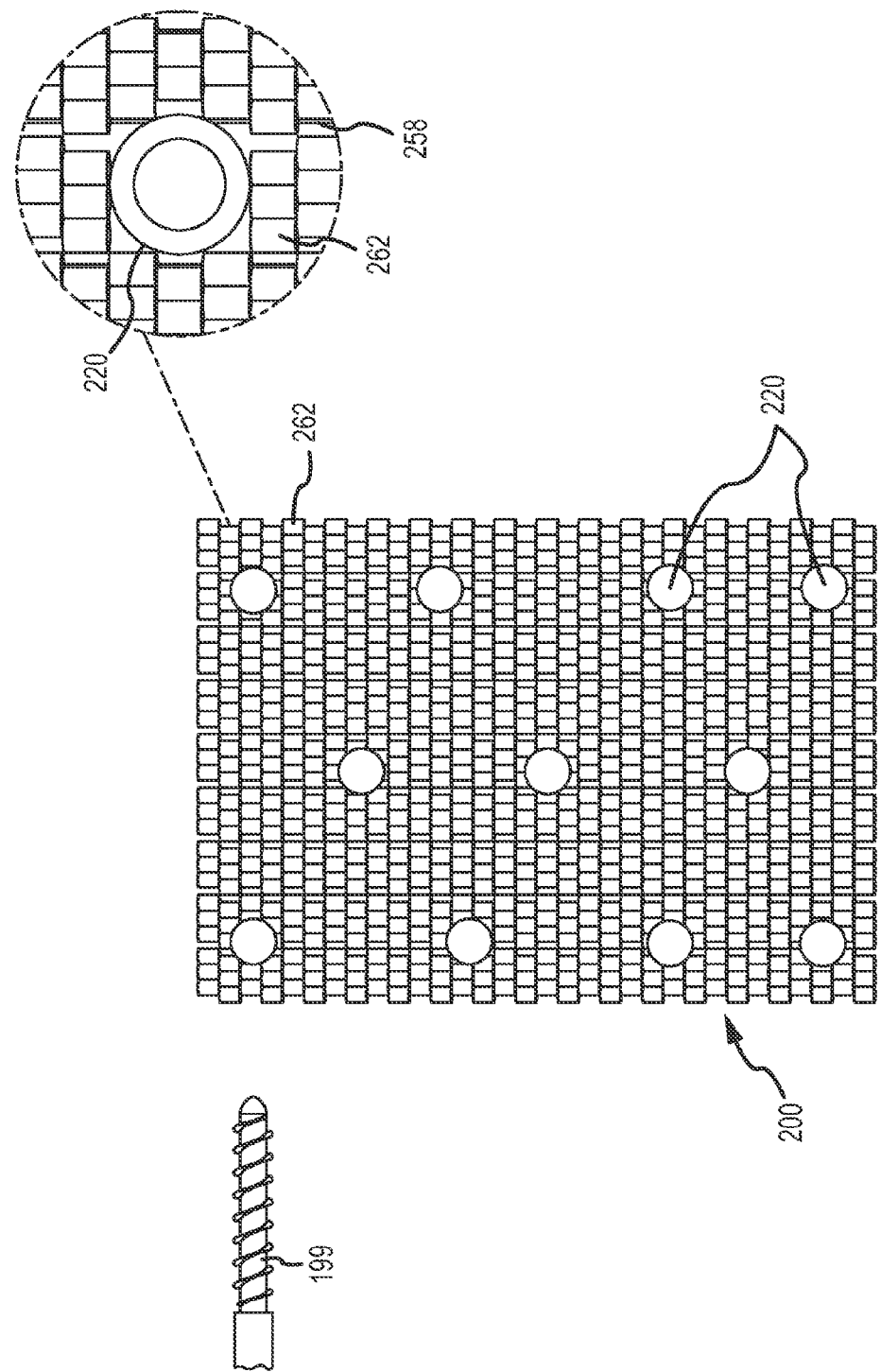
FIG. 2 is a top plan view of one embodiment of the present invention.

FIG. 2 depicts another embodiment of the present invention 200, where a plurality of apertures, eyelets, or grommets 220 are provided within a space defined by the generally cylindrical components 262. FIG. 2 displays one embodiment of the present invention wherein numerous cylindrical components 262 are provided. One of skill in the art will recognize that the present invention is not limited to any particular size or number of generally cylindrical components 262. The size and quantity of these components 262 may vary according to size of the patient, area in which the device 200 is to be applied, etc.

Grommets 220 provide for points of attachment for surgical screws 199 and further facilitate the conformity of the device 200 to various non-planar regions. One of skill in the art will recognize that any number of these grommets 220 may be used (i.e. provided with a pin, screw or anchor) or left unutilized. Where grommets 220 are provided which are not used, it will be recognized that these unused grommets 220 constitute empty spaces which further facilitate mass transfer through the device. Thus, in one embodiment, no further action need to be taken where the grommets 220 are not used. In an alternative embodiment, plugs or fillers (not shown) may be disposed within undesired grommets 220. Such plugs may be comprised of a material that is compatible with the material comprising the implant 200.

FIG. 2 further includes a call-out illustrating how grommets 220 may be incorporated into the wire 258/cylinder 262 network of the present invention. As will be recognized, grommets 220 must comprise more than a mere hole formed through a fabric or woven network. Thus, grommets 220 are provided which provide for points of attachment with wires 258.

Figure 3:
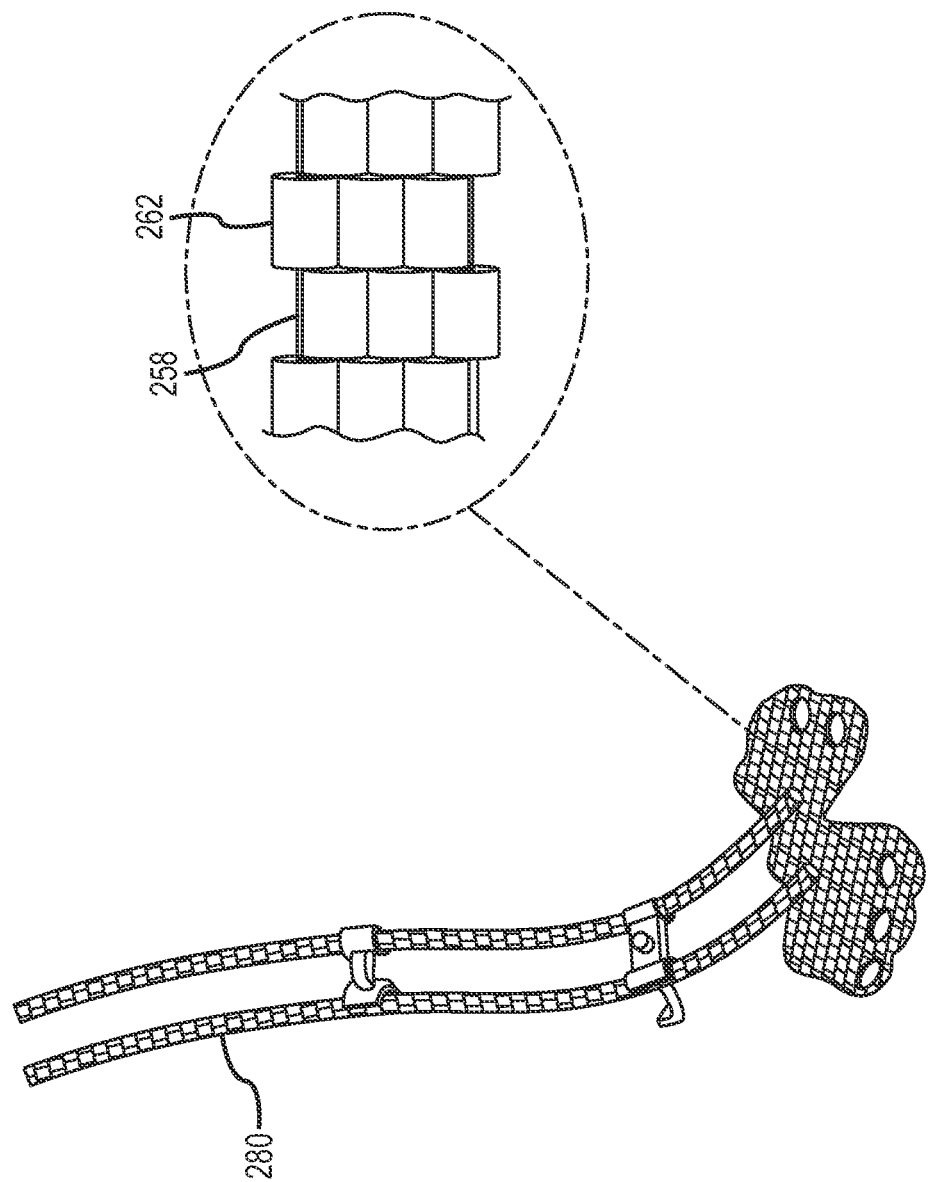
FIG. 3 is an isometric view of one embodiment of the present invention.

FIG. 3 depicts one embodiment of the present invention where a spinal rod is modified and comprises generally cylindrical components of the present invention. For example, cylindrical components 262 may comprise a portion of the device intended to interface with bone. Providing these components 262 in at least portions of such a device offers advantages of being improved bone growth within and around aspects of the device. Although FIG. 3 is shown with features of the present invention incorporated into a rod fixation system, it will be recognized that these features may be incorporated into a variety of surgical implants where it is necessary or desirable to allow for increased bone and tissue growth underneath an implant or an area immediately surrounding an implant.

Figure 4:
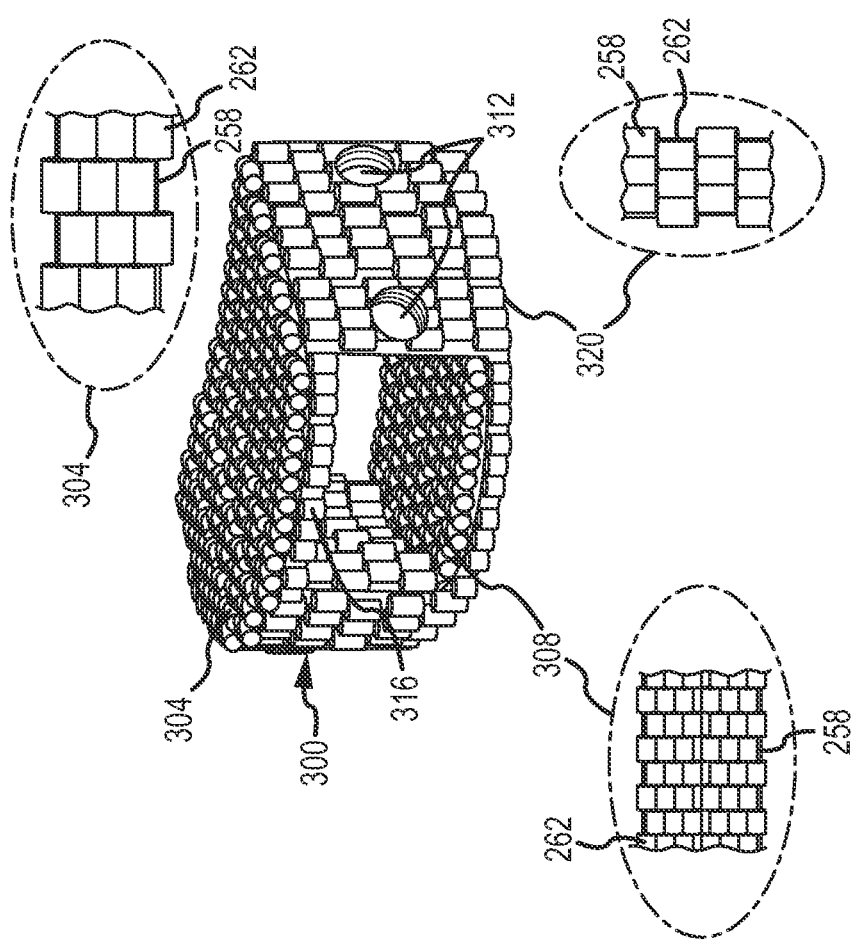
FIG. 4 is an isometric view of one embodiment of the present invention.

FIG. 4 depicts an embodiment of the present invention wherein portions of a spinal implant cage 300 comprise generally cylindrical components 262 and allows for bone growth and osteosynthesis through at least a portion of the cage. For example, surfaces 304, 308 of a spinal implant cage may be comprised of an array of generally cylindrical components 262 to allow for bone growth and/or resorbtion through these portions 304, 308. Where generally cylindrical components 262 disposed on wires 258 are to be implemented in a portion of a device 316 that spans a distance, the device and array of cylindrical components 262 may need to withstand certain amounts of forces applied in bending or moment. Those of ordinary skill in the art will recognize that varying the thickness and/or gauge of the wires 258 employed will allow for the device to accommodate smaller or larger amounts of bending moment. Those of skill in the art will recognize that both portions 304, 308 of a spinal implant cage need not comprise the same size, number, or arrangement of generally cylindrical components 262. Indeed, a cage with a different composition of generally cylindrical components 262 on a top 304 and bottom 308 portion of is contemplated as within the scope of the present invention.

As further shown in FIG. 4, sidewall portions 320 of a spinal implant cage may also be comprised at least partially of a stacked arrangement of generally cylindrical components 258. Sidewall portions 320 of an implantable cage may further comprise apertures 312 through which screws may be placed or which simply allow for transmission of certain fluids, or both. In one embodiment, when cylindrical components 258 are stacked to form portions of a sidewall 320, the cylinders 258 may be oriented so that their longitudinal axis is generally perpendicular with a longitudinal axis of a human spine (not shown) in which the implant is to be placed. Thus, when compression forces are applied due to gravity, activity, or general load bearing on the spine, the stacked arrangement is capable of accommodating compression forces. It will be recognized that the buckle strength of such an arrangement will be dependent upon a number of factors, including, for example, strength of the cylinders, length of the cylinders, overall height of the implant, spacing between wires 262, gauge and strength of the wires, material properties, and other factors. Thus, the dimensions and characteristics of the cage may be tailored by altering these factors as will be apparent to one of skill in the art for the size and type of patient in which such a cage or similar device will be utilized.

Generally cylindrical components as shown in FIG. 4 and as will be recognized by those of skill in the art may be bounded by any number of features. For example, cylinders 258 may be bounded and generally held in position by end plates as described herein or by any number of other similar devices. Cylinders 258 may be bounded by, for example, main body portions of an implantable cage which define the maximum longitudinal distance with which a cylinder can travel.

Figure 5:
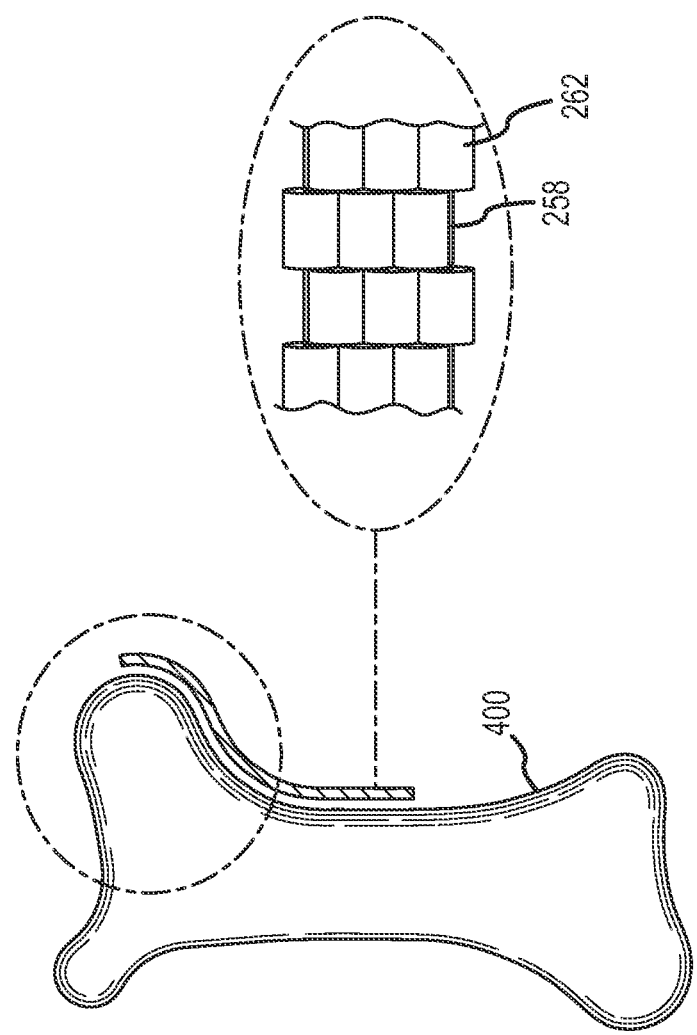
FIG. 5 is an elevation view of one embodiment of the present invention.

FIG. 5 depicts a possible application of the present invention 200 to a non-planar implant site. As shown, a bone 400 to which various embodiments of the present invention may be applied is not necessarily flat or planar. Aspects of the present invention, including malleable or flexible wires (not shown) and corresponding generally cylindrical components are provided which allow for the present invention 200 to be manipulated by a user and conform to a variety of different surfaces. A main portion of the device 200 is provided that further allows for the transfer of mass, such as blood, fluid, and air, to and from an underlying portion of the bone 300 to be repaired. It will be recognized that the present invention may be applied to such a non-planar site 400 in a variety of orientations. For example, in FIG. 5, the implant may be applied with rollers 262 disposed so that a longitudinal axis of the rollers 262 is perpendicular to a longitudinal axis of the bone 400. Alternatively, the invention may be applied with a longitudinal axis of the rollers 262 being parallel to a longitudinal axis of the bone 400 and wrapped around at least a portion of the circumference of a bone 400. It will further be recognized that size and quantity of rollers 262, as well as the dimensions and properties of the wires 258 may be adjusted so as to achieve the most appropriate fit to the workspace.

Figure 6:
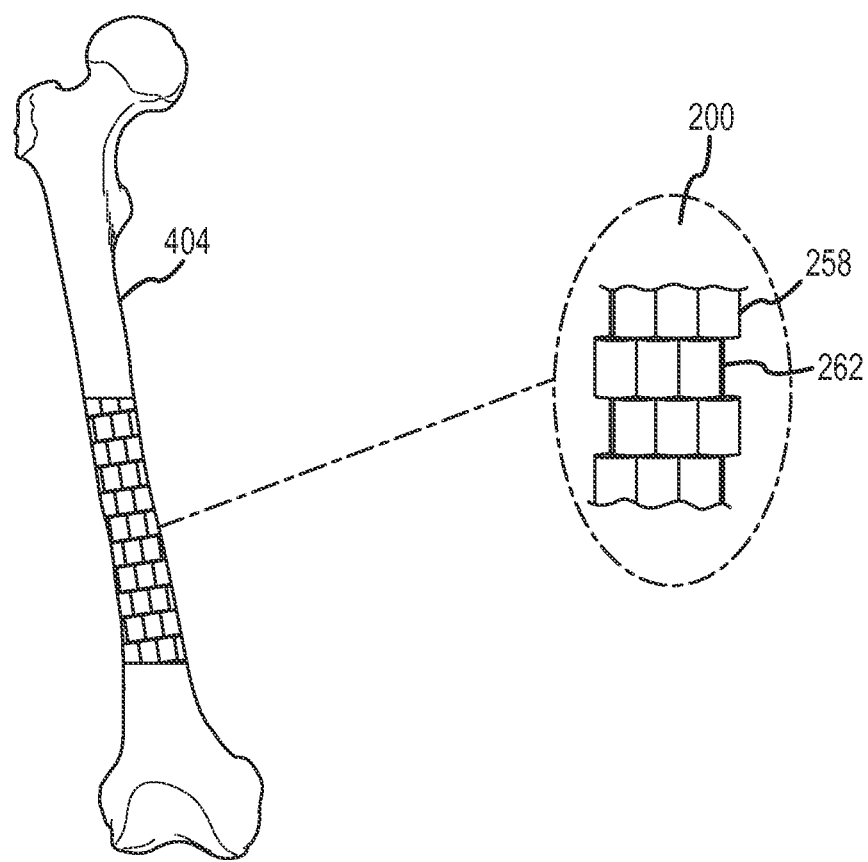
FIG. 6 is an elevation view of one embodiment of the present invention.

FIG. 6 depicts one embodiment of the present invention wrapped or drawn around a surgical work site. As shown, embodiments of the present invention may be wrapped around the circumference of a bone 404 to secure, for example, a fracture site while still allowing for mass transfer to the bone 404. Although FIG. 6 shows this aspect of the present invention with respect to fracture-type application, the present invention contemplates various other uses of such a device, including, but not limited to, applications in spinal fixation procedures.

Figure 7:
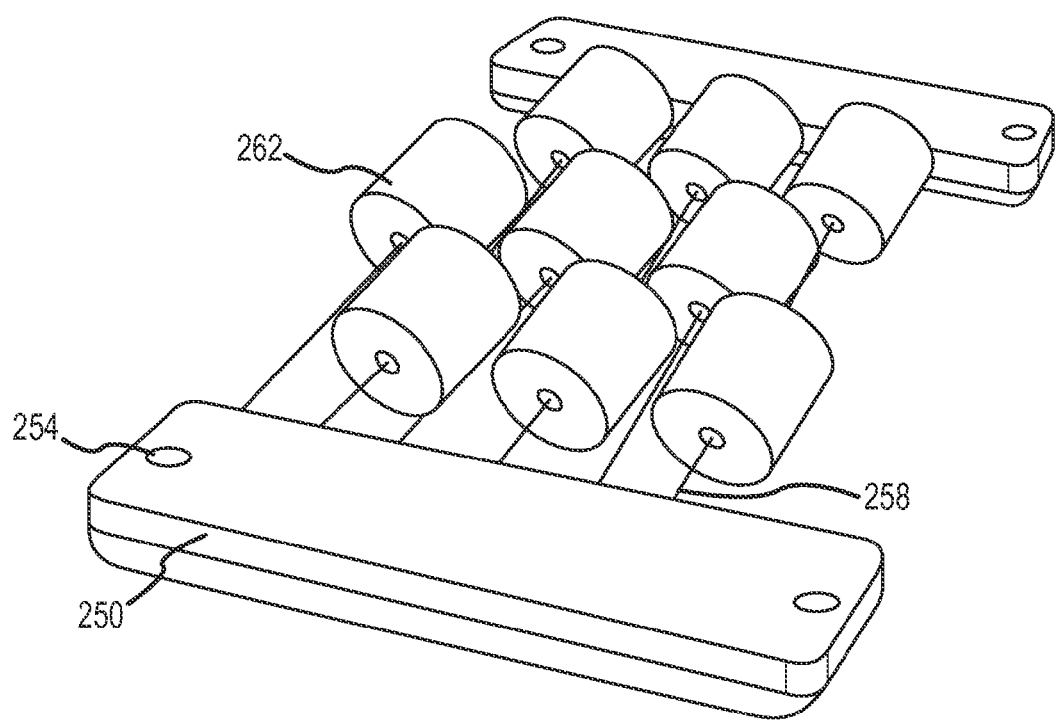
FIG. 7 is an isometric view of one embodiment of the present invention.

FIG. 7 is an isometric view of one embodiment of the present invention, showing cylinders 262, wires 258, through holes 254 and end plates 250. The drawing is not necessarily to scale and various dimensions of the embodiment shown in FIG. 7 may be altered, adjusted, and modified based upon specific needs and desired uses of the invention. The present invention offers numerous advantages of known braided mesh devices. Particularly, the stacked arrangement contemplated by the present invention allows for the accommodation of greater forces and reduced risks of separation or failure while still providing a device that is capable of conforming to a variety of non-planar surfaces. Thus, non-braided embodiments of the present as shown and described herein offer advantages to both patients and surgeons.

Figure 9:
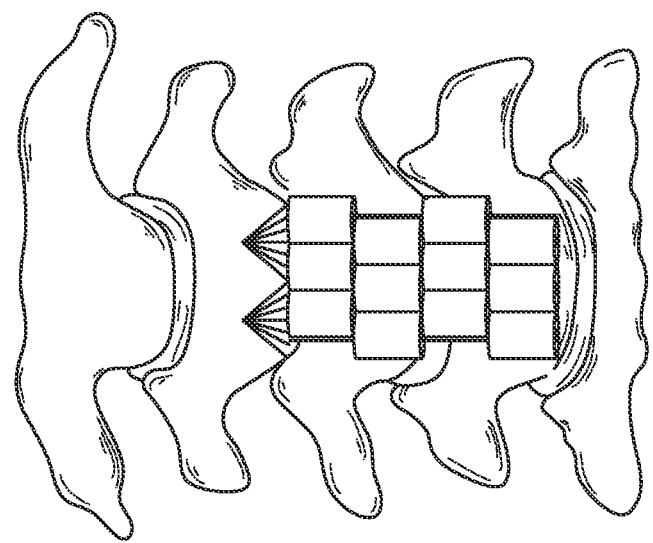
FIG. 9 is an elevation view of one embodiment of the present invention.
Figure 8:
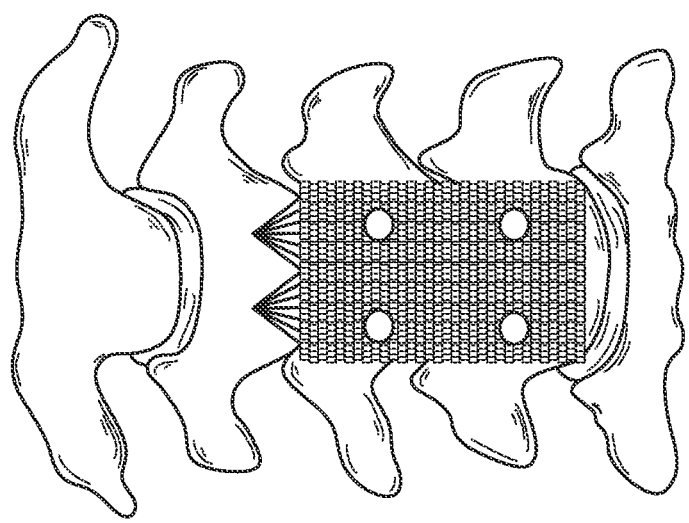
FIG. 8 is an elevation view of one embodiment of the present invention.
Figure 10:
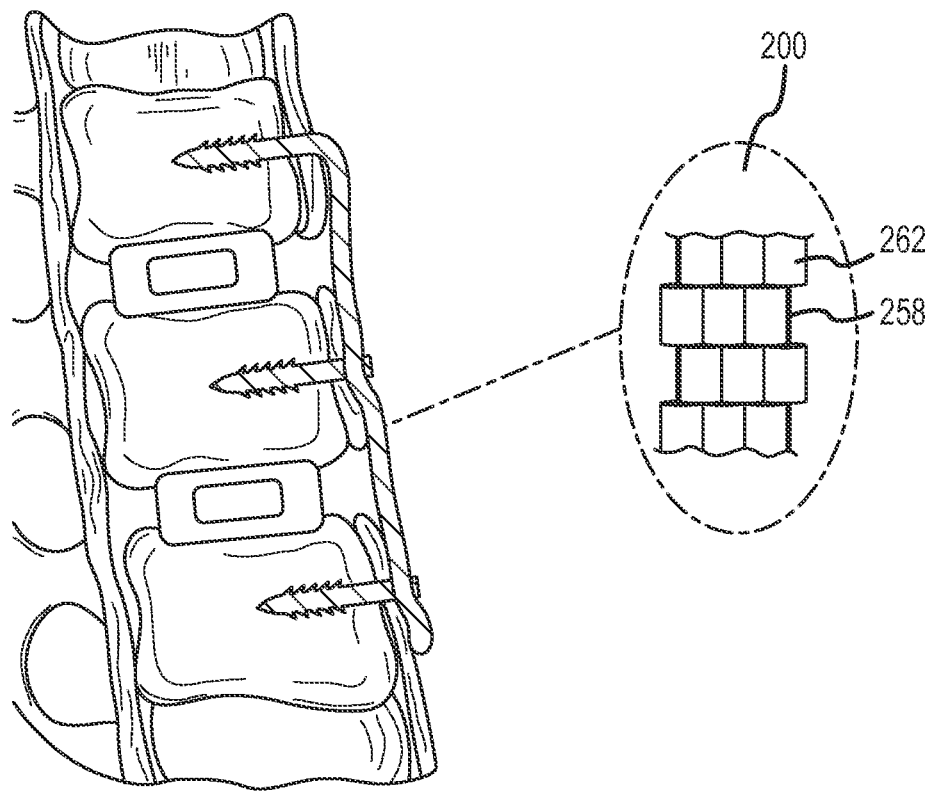
FIG. 10 is a side elevation view of one embodiment of the present invention.

FIGS. 8-10 show one embodiment of the present invention for use in spinal fusion procedures. Spinal fusion typically requires posterior fixation devices to achieve stability and rigidity. However, in these procedures, it is often advantageous to utilize low-profile devices for posterior fixation (and similar procedures) which are furthermore biocompatible and foster growth and development of bone and tissue disposed beneath and/or proximal to the device. Thus, devices as shown and described herein may be utilized to provide a generally conformable device for use in spinal fusion procedures. Furthermore, in one embodiment, these devices comprise shoulderless attachment features which allow for devices of the present invention, such as bone screws or pins, to be fully driven into the vertebral surfaces. Thus, low-profile secure attachment is achieved in spine stabilization procedures. Attachment devices and locations may reside within an area defined by generally cylindrical components of the present invention, and/or may reside within endplates or various extensions of the present invention.

FIG. 10 depicts a side elevation view of one embodiment of the present invention showing various a dynamic implants anchored to a spine at a plurality of locations. Anchoring devices and apertures for receiving anchoring devices may be provided as shown and described in the present disclosure. For example, apertures or grommets may be provided at predetermined locations which correspond to vertebral spacing (i.e. for a given patient size and/or location along the spine) or may be provided at a variety of locations on the device. In one embodiment, a plurality of such grommets is provided which may be utilized or disregarded at a user's discretion.

Figure 11:
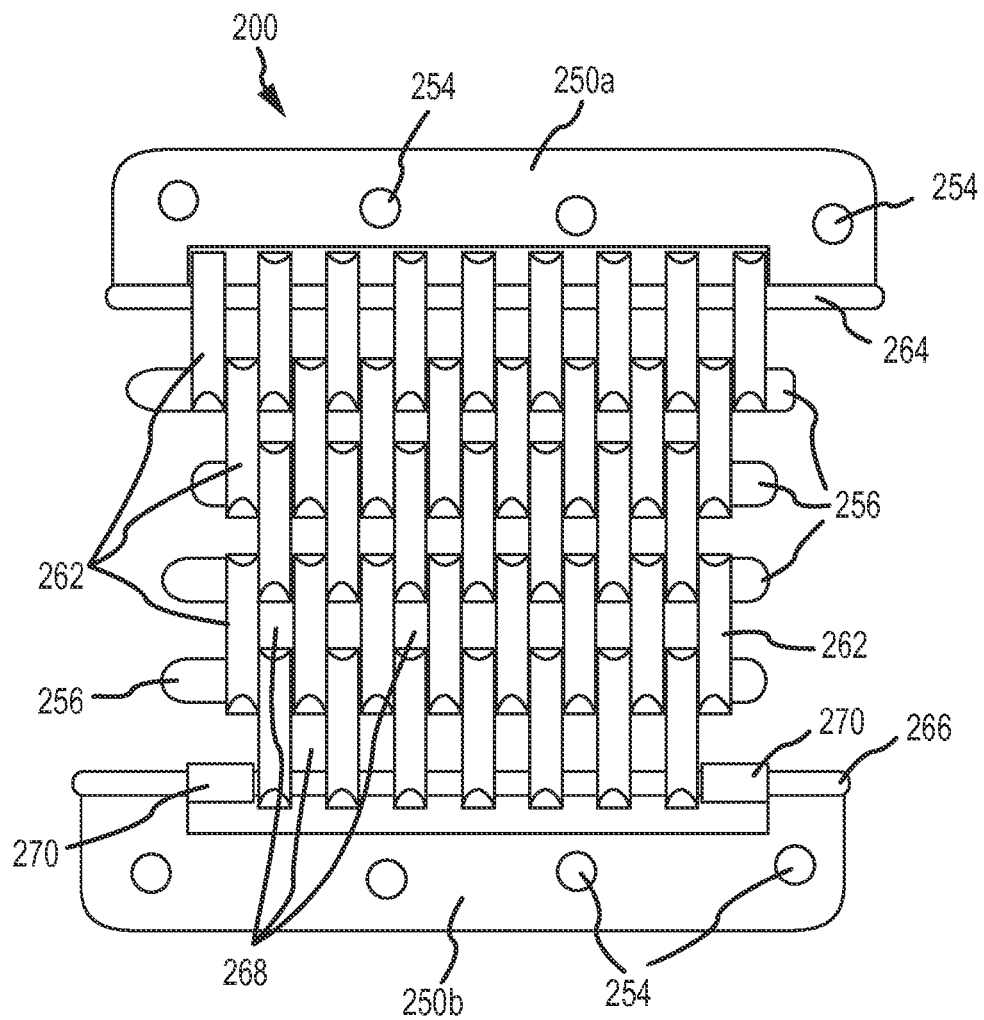
FIG. 11 is a top plan view of one embodiment of the present invention.

FIG. 11 shows an alternative embodiment of a surgical implant 200 according to the present invention wherein pins 256 and generally uniform members 262 form an interlocking mesh. In the depicted embodiment, a plurality of pins 256 comprise a longitudinal axis oriented substantially perpendicular to a longitudinal axis of generally uniform members 262. The generally uniform members 262 have a first aperture and a second aperture which allow at least one pin 256 to perpendicularly pass through at least one end of the generally uniform member 262 such that the generally uniform members 262 are rotatable about at least one pin 256.

A first pin 254 is affixed to a first end plate 250a, and a second pin 266 is affixed to a second end plate 250b. The end plates 250a, 250b comprise through holes 254 which allow the end plates 250a, 250b to be affixed to an anatomical feature, such as bone or tissue. As shown in FIG. 11, each of the pins 256 extend substantially perpendicularly through at least one end of at least one generally uniform member 262. The pins 256 provide resistance to bending and moment forces, while generally uniform members 262 are allowed to rotated about pins 256. Pins 256 are moveable with respect to another (at least when the insert 200 is an in unsecured state). Adjacent pins 256 are spaced apart from one another by a distance approximately equal the length of the adjoining uniform members 262 which are substantially rigid objects. Adjacent and parallel uniform members 262 are generally separated by a distance approximately equal to a width of a uniform member 262.

In some embodiments, spacers 270 are provided to generally restrain movement of members 262. Spacers 270 may be obviated, however, by the provision of an additional pin 256 and row of members 262 (i.e. where the pattern shown in FIG. 11 is extended downward by an additional row).

The embodiment shown in FIG. 11 provides for a plurality of void spaces 268, at least between staggered or adjacent uniform members 262, for allowing and promoting growth and fusion of materials as is known to be advantageous in securing, repairing, and healing associated with an injury or surgical site. The mesh insert 200 also provides, however, desirable resistances to certain forces while being capable of wrapping or molding around uneven surfaces.

Figure 12:
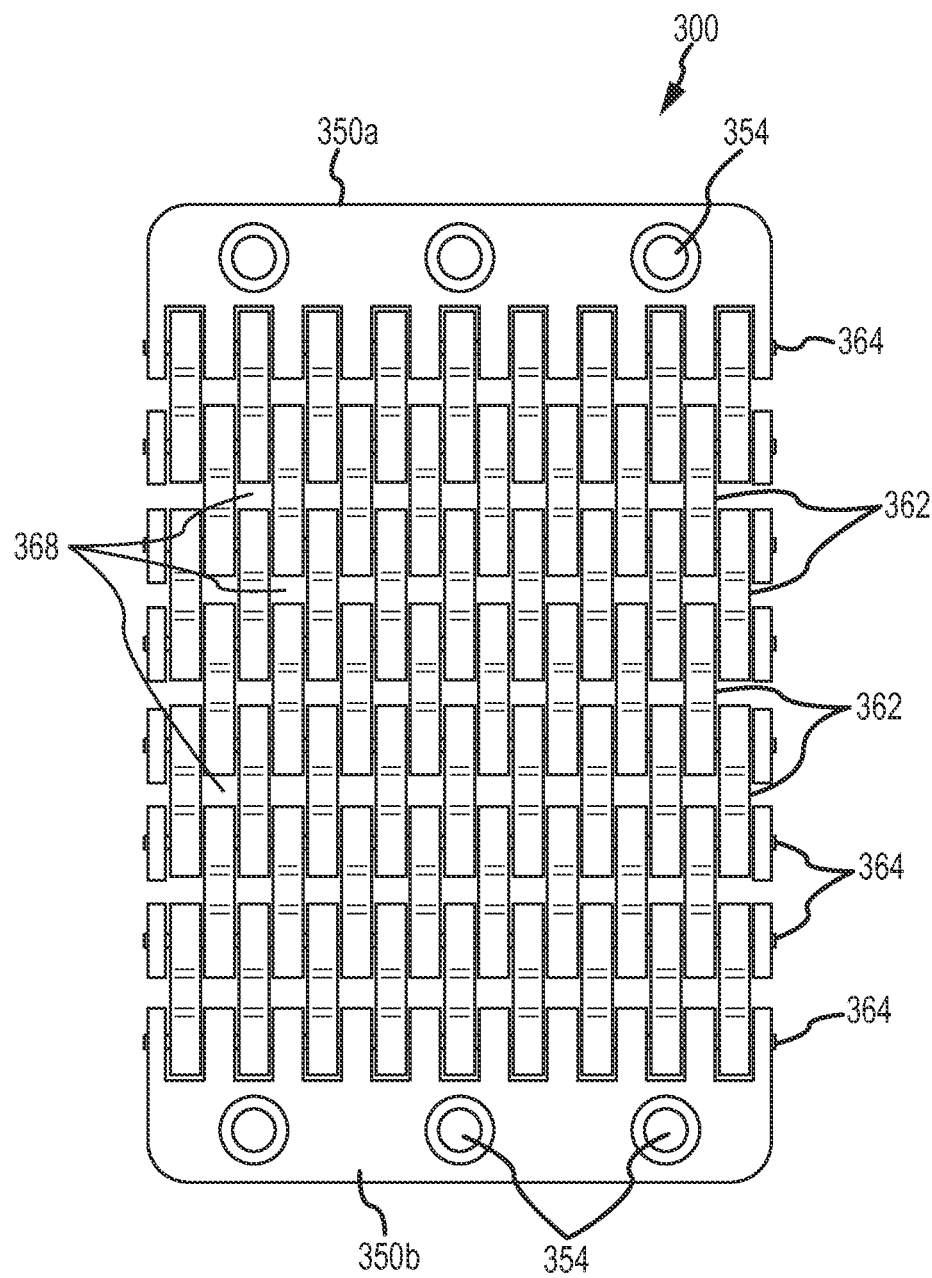
FIG. 12 is a top plan view of one embodiment of the present invention.

FIG. 12 shows an alternative embodiment of a surgical implant 300 according to the present invention wherein through-pins 364 and arcuate members 362 form an interlocking mesh. In the depicted embodiment, a plurality of pins 364 comprise a longitudinal axis oriented substantially perpendicular to a longitudinal axis of arcuate members 362. In certain embodiments, pin members 364 comprise substantially rigid members for resisting bending under moment forces. In alternative embodiments, pins 364 comprise flexible members, more preferably with memory characteristics such that flexibility is elastic and the members return to a substantially straight orientation when bending forces are not applied. Flexible members provide additional wrapping functionality to the device. In one embodiment, the pins 364 comprise stainless steel cables with an elastic or restoring force such that the device is bendable or flexible. As will be recognized by one of ordinary skill in the art, the arcuate members 362 form an interlocking mesh such that bending or articulation of the device is at least partially restricted. As will be further recognized, such restriction will be a function of the spacing and size of the arcuate members 362, as well as the stiffness or rigidity (or lack thereof) of the pins 364. The arcuate members 362 have a first aperture and a second aperture which allow at least one pin 364 to perpendicularly pass through at least one end of the link members 362 such that the arcuate members 362 are rotatable about at least one pin 364.

A first pin 364 is affixed to a first end plate 350a, and a second pin 364 is affixed to a second end plate 350b. The end plates 350a, 350b comprise through holes 354 which allow the end plates 350a, 350b to be affixed to an anatomical feature, such as bone or tissue. End plates of the present invention are not limited to plates comprising a specific number of holes. Although certain embodiments contemplate providing at least two through holes in each end plate, it will be recognized that any number of apertures or through holes may be provided. In one embodiment, three through holes 354 are provided in the end plate, and a plurality of additional holes are provided as cut-outs to reduce the overall weight of the device 300. As shown in FIG. 12, each of the pins 364 extend substantially perpendicularly through at least one end of at least one arcuate member 362. The pins 364 provide resistance to bending and moment forces, while arcuate members 362 are allowed to rotated about pins 364. Pins 364 are moveable with respect to another (at least when the insert 300 is an in unsecured state). Adjacent pins 364 are spaced apart from one another by a distance approximately equal the length of the adjoining uniform arcuate members 362 which are substantially rigid objects. Adjacent and parallel uniform arcuate members 362 are generally separated by a distance approximately equal to a width of a uniform arcuate member 362.

The embodiment shown in FIG. 12 provides for a plurality of void spaces 368, at least between staggered or adjacent arcuate members 362, for allowing and promoting growth and fusion of materials as is known to be advantageous in securing, repairing, and healing associated with an injury or surgical site. The insert 300 also provides, however, desirable resistances to certain forces while being capable of wrapping or molding around uneven surfaces.

Figure 13:
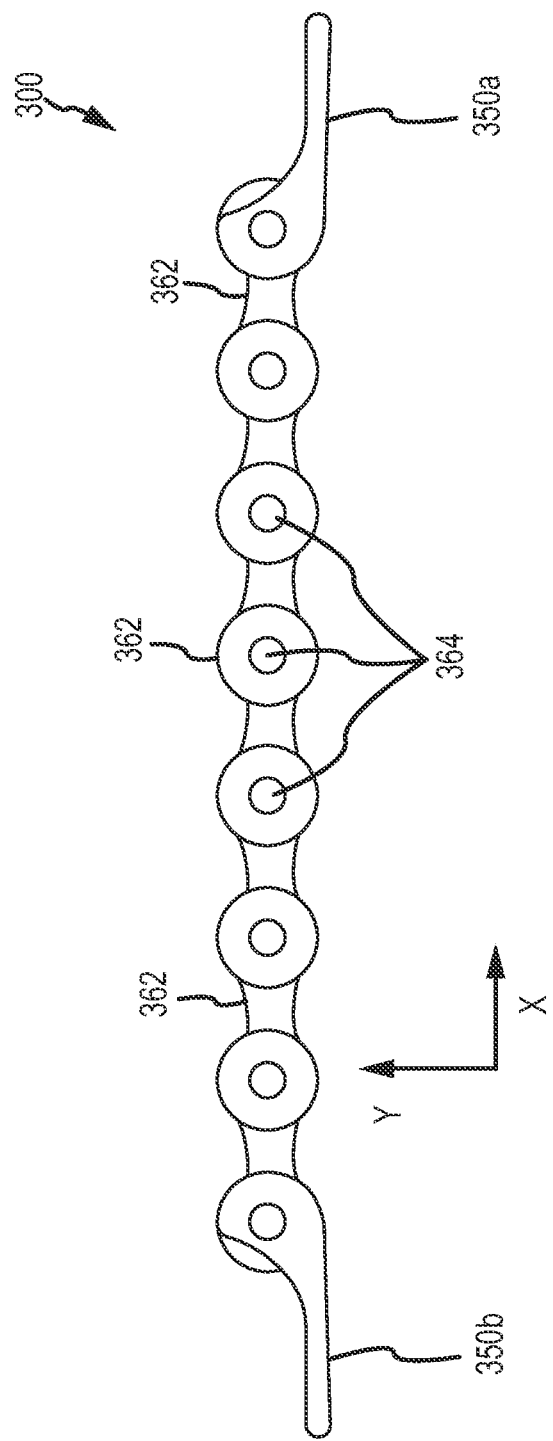
FIG. 13 is a side elevation view of one embodiment of the present invention.

FIG. 13 is a side elevation view of the embodiment of FIG. 12 depicting the surgical implant 300. As shown, the implant 300 comprises opposing end plates 350a, 350b and a plurality of arcuate members 362 provided therebetween. A plurality of arcuate members 362 are interconnected to end plates 350a, 350b and additional arcuate members 362 via pins 364. In the depicted embodiment, link members 362 comprise arcuate profiles similar to roller chain members and comprising a first through hole proximal a first end and a second through hole proximal a second end, each of the through holes adapted for receiving a pin member 364 and allowing rotation of the arcuate member 362 about the pin member 364. The arcuate members 362 and the device 300 are capable of rotation about the axis of the pins 364 such that the device 300 can wrap around one or more anatomical features. That is, as shown in FIG. 13, the device is adapted to rotate about a first axis while generally resisting deformation or rotation about the X and Y axis depicted in FIG. 13. In certain embodiments, pins 364 as provided as substantially flexible members such that bending or deformation of the implant 300 about the X and/or Y axis is at least partially permitted.

Figure 14:
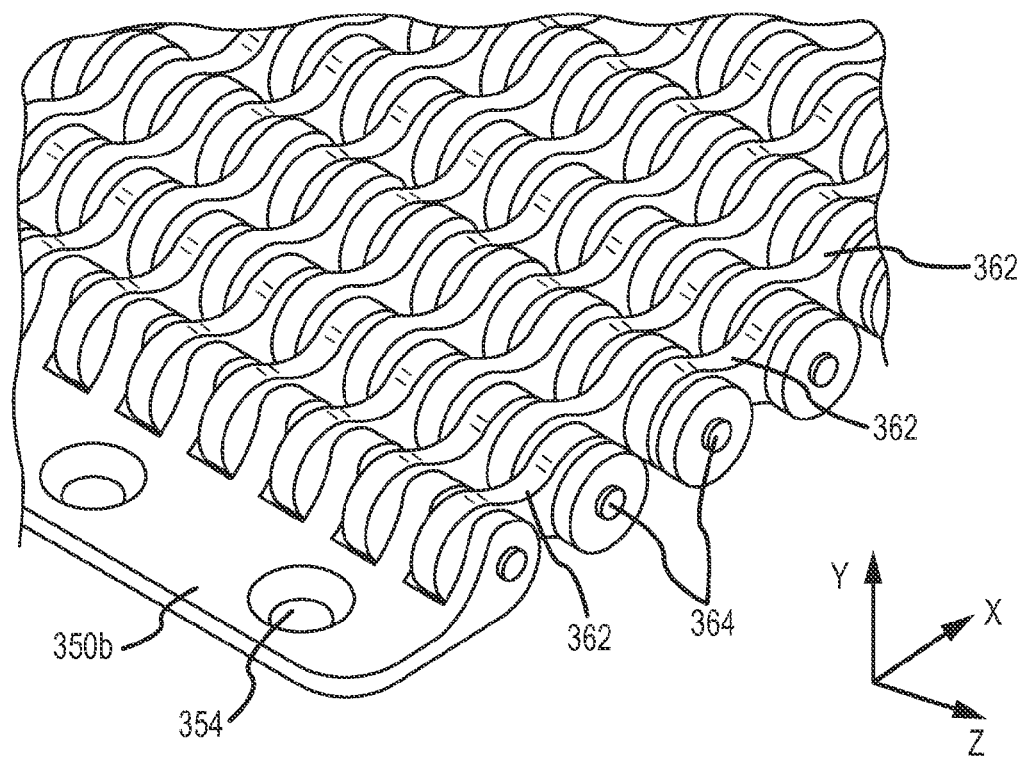
FIG. 14 is a perspective view of one embodiment of the present invention; The drawings are not necessarily to scale.

FIG. 14 is a perspective view of the embodiment of FIGS. 12-13 comprising anchor plate 350, arcuate link members 362 and pin members 364. As shown, the link members 362 are provided in alternating rows to form a dynamic implant 300. A primary axis of rotation Z for the link members is provided, the axis being substantially perpendicular to the longitudinal axis of the pin members 364. In various embodiments, link members 362 comprise a predetermined length of between approximately 0.25 inches and approximately 1.00 inches. In preferred embodiments, link members 362 comprise a length of between approximately 0.40 inches and approximately 0.75 inches. In one embodiment, link members comprise a length of 0.65 inches, with a distance between through holes of approximately 0.435 inches. It will be understood, however, that implants 300 of the present invention are not limited to any particular size or proportions. Indeed, various different sized implants are contemplated as within the scope and spirit of the present invention, particularly where different sized implements are desired for different anatomical features.

In various embodiments, pin members 364 comprise flexible members that permit various deformations of the implant 300. In addition to the permitted rotation of the arcuate members 362 with respect to pins 364 as well to additional arcuate members 362, the device 300 may deform or rotate about the X axis. While various embodiments contemplate providing substantially flexible pin members in combination with arcuate members and substantially rigid opposing plate members, alternative embodiments contemplated providing deformable or flexible plate members. Such embodiments may be desirable in various applications, such as where the device 300 is intended to be wrapped around or secured to a generally cylindrical bone or similar anatomical feature. In certain embodiments, sufficient spacing is provided in the through holes of the arcuate members 362 such that movement of the arcuate member relative to the pin provided therethrough is allowed. Additionally, the collective movement of the arcuate members with respect to associated pin members further allows the device to expand or contract.

Figure 15:
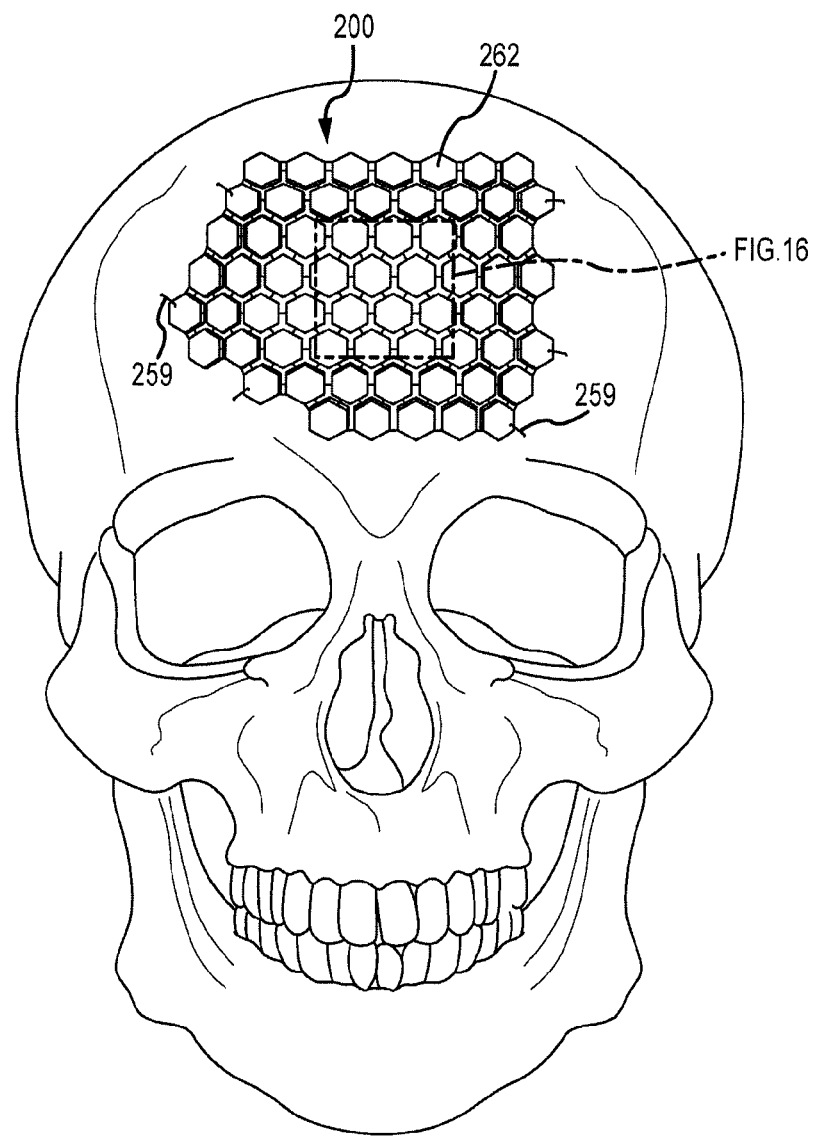
FIG. 15 is a perspective view of one embodiment of the present invention illustrating the arrangement between elements (polygonal) and wires, as well as connecting members (e.g., staples).

FIG. 15 is a perspective view of one embodiment of the present invention illustrating the arrangement between elements (polygonal) and wires, as well as connecting members 259 (e.g., staples).

Figure 16:
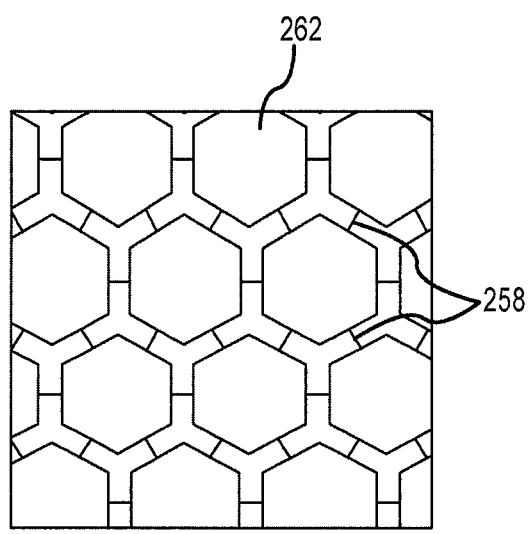
FIG. 16 is a close up plan view of one region of the surgical implant device pictured in FIG. 15, showing the plurality of wire members and plurality of generally uniformly shaped members forming a malleable mesh-like surface structure.

FIG. 16 is a close up plan view of one region of the surgical implant device 200 pictured in FIG. 15, showing the plurality of wire members 258 and plurality of generally uniformly shaped members 262 forming a malleable mesh-like surface structure.

While various embodiments of the present invention have been described in detail, it is apparent that modifications and alterations of those embodiments will occur to those skilled in the art. However, it is to be expressly understood that such modifications and alterations are within the scope and spirit of the present invention, as set forth in the Summary, Detailed Description, and in the following claims. Further, the invention(s) described herein are capable of other embodiments and of being practiced or of being carried out in various ways. In addition, it is to be understood that the phraseology and terminology used herein is for the purposes of description and should not be regarded as limiting. The use of "including," "comprising," or "adding" and variations thereof herein are meant to encompass the items listed thereafter and equivalents thereof, as well as, additional items.

What is claimed is:

1. A surgical implant device comprising: a plurality of elongate wire members spaced generally parallel to each other to form adjacent rows; a plurality of generally uniformly shaped members connected to said plurality of elongate wire members, wherein a first generally uniformly shaped member has a flat top end and a flat bottom end, and has at least two elongate wire members connected thereto, and a second generally uniformly shaped member has a flat top end and a flat bottom end and has at least two elongate wire members connected thereto, wherein said plurality of elongate wire members and plurality of generally uniformly shaped members form a malleable mesh-like surface structure that permits liquids to flow therethrough, enabling bone and tissue growth beneath, around, and/or within the implant device, said mesh-like surface structure being malleable and adapted to conform to a variety of non-planar implantation sites to provide sufficient stability and structural support to the area sought to be covered by said surgical implant, wherein said plurality of elongate wire members have a diameter of approximately between 0.010 mm and 2.00 mm, a length of at least about 3 cm, and said implant device having a plurality of openings consisting of spatial gaps between said generally uniformly shaped members, said openings organized in rows or columns, said openings allowing bone growth material to grow through at least a portion of the implant device, and said implant device having a plurality of bone screw receiving holes adapted to accommodate surgical screws.

2. The device of claim 1, wherein said implant device has a load supporting capacity in a first direction and a flexibility that permits twisting of said device in a direction perpendicular to said first direction, said wires made of a malleable and/or flexible metal and have sufficient strength to resist tension forces and have thin enough gauges to allow for shaping of the device by hand to allow a surgeon to contour the device to an appropriate curvature of an anatomic shape.

3. The device of claim 1, wherein said implant device has a bottom surface for placement against bone portions, said bottom surface having a convex shape along a longitudinal axis of said generally uniformly shaped members adapted for contacting the bone surface of a patient to promote healing of the bone surface and surrounding bone and/or tissue.

4. The device of claim 1, wherein the generally uniformly shaped members are made of a material selected from the group consisting of surgical stainless steel, titanium, silicon, glass, quartz, plastic, metal and metal alloys, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, SiO1, SiO2, silicon carbide, silicon nitride, polyacrylonitrile (PAN), polyetherketone, polyetheretherketone (PEEK), polyimide, an aromatic polymer, and an aliphatic polymer.

5. The device of claim 1, wherein the generally uniformly shaped members are generally arcuate in shape.

6. The device of claim 1, wherein said generally uniformly shaped members comprise bioresorbable material.

7. The device of claim 1, wherein a bioactive coating is on said generally uniformly shaped members, said coating comprising fusion promoting bone morphogenetic proteins.

8. The device of claim 1, wherein said device is adapted to cover a surgery site.

9. The device of claim 1, wherein the generally uniformly shaped members have a first side adapted to face toward a bone and a second side for facing away from a bone.

10. The device of claim 1, wherein the generally uniformly shaped members together form a pattern that permits liquids to flow therethrough and permits bone ingrowth.

11. The device of claim 1, wherein said device further comprises a connecting member selected from the group consisting of staples, fasteners, clasps, sutures, pins, zippers, welds, and crimping elements adapted for use with an appliance or implant.

12. The device of claim 1, wherein said device comprises a pliable structure having a first face side and a bone interface side, said bone interface side including a multiplicity of recesses that permit ingrowth of bone therethrough.

13. The device of claim 1, wherein the generally uniform shaped members are interconnected to said wire members and together form a pattern to facilitate bone and tissue regeneration.

14. The device of claim 1, wherein said elongate wire members comprise one of ceramic, titanium, stainless steel, stainless steel alloys and titanium alloys.

15. The device of claim 1, wherein said device does not prevent the transfer of air, blood, and fluid and facilitates healing and repair of bone.

16. The device of claim 1, wherein said device is adapted to be integrated with ingrown osseous tissue.

17. The device of claim 1, wherein said device comprises one of resorbable synthetic materials and organically degradable polymers.

18. The device of claim 1, wherein said device is coated with one of fusion promoting chemical substances and bone morphogenetic proteins.

19. The device of claim 1, wherein said generally uniformly shaped members comprise polygonal structures.

20. The device of claim 1, wherein said generally uniformly shaped members have surfaces that are roughened to enhance bone growth.

* * * * *